(12) United States Patent
Von Schuckmann

(10) Patent No.: US 10,478,573 B2
(45) Date of Patent: Nov. 19, 2019

(54) COUNTER AND HANDHELD DEVICE WITH COUNTER

(71) Applicant: Alfred Von Schuckmann, Kevelaer (DE)

(72) Inventor: Alfred Von Schuckmann, Kevelaer (DE)

(*) Notice: Subject to any disclaimer, the term of this patent is extended or adjusted under 35 U.S.C. 154(b) by 764 days.

(21) Appl. No.: 15/026,270

(22) PCT Filed: Oct. 7, 2014

(86) PCT No.: PCT/EP2014/071427
§ 371 (c)(1),
(2) Date: Mar. 31, 2016

(87) PCT Pub. No.: WO2015/055463
PCT Pub. Date: Apr. 23, 2015

(65) Prior Publication Data
US 2016/0250425 A1 Sep. 1, 2016

(30) Foreign Application Priority Data

Oct. 15, 2013 (DE) .................. 10 2013 111 381
Oct. 6, 2014 (DE) .................. 10 2014 114 462

(51) Int. Cl.
*A61M 15/00* (2006.01)
*G06M 1/04* (2006.01)
*G01F 11/42* (2006.01)

(52) U.S. Cl.
CPC .... *A61M 15/0075* (2014.02); *A61M 15/0025* (2014.02); *G01F 11/42* (2013.01); *G06M 1/041* (2013.01)

(58) Field of Classification Search
CPC .............. A61M 15/00; A61M 15/0021; A61M 15/0025; A61M 15/0068; A61M 15/007;
(Continued)

(56) References Cited

U.S. PATENT DOCUMENTS 6,283,365 B1  9/2001 Bason
7,448,342 B2  11/2008 Von Schuckmann
(Continued)

FOREIGN PATENT DOCUMENTS

DE        100 61 723 A1    7/2002
DE    10 2005 033398 A1    5/2006
(Continued)

OTHER PUBLICATIONS

International Search Report of PCT/EP2014/071427, dated Feb. 4, 2015.

*Primary Examiner* — Colin W Stuart
*Assistant Examiner* — Matthew D Ziegler
(74) *Attorney, Agent, or Firm* — Collard & Roe, P.C.

(57) ABSTRACT

A counter for a handheld device for dispensing a pharmaceutical substance includes at least one counter wheel having legible characters. The counter wheel is rotatable about a rotational axis, and a drive part having a shaped engagement section rotates the counter wheel. An acting part, displaceable relative to the counter wheel in the direction of extension of the rotational axis against a spring force, is connected to and rotates together with the drive part. A base part which can form a part of the housing and can be inserted into the housing at least partly overlaps the substance container in the direction of the longitudinal axis of the substance container, and has a stationary rotational axis for the counter wheel, the drive part preferably being guided in the rotational axis. The drive part is located on the side of the substance container with respect to the counter wheel.

24 Claims, 24 Drawing Sheets

(58) Field of Classification Search
CPC .......... A61M 15/0071; A61M 15/0065; A61M 15/0073; A61M 15/0076; A61M 15/0078; A61M 15/009; A61M 11/00; A61M 11/006; A61M 11/007; A61M 11/06; A61M 11/08; A61M 13/00; A61M 2205/33; A61M 2210/0625; G01F 11/00; G01F 11/42; G01F 15/001; G01F 15/002; G01M 1/041
USPC ............ 128/205.23; 116/299, 284, 308, 309, 116/285, 298
See application file for complete search history.

(56) References Cited

U.S. PATENT DOCUMENTS

| | | | |
|---|---|---|---|
| 7,510,100 B2 | 3/2009 | Stradella et al. | |
| 7,827,984 B2 | 11/2010 | Von Schuckmann | |
| 2004/0211420 A1* | 10/2004 | Minshull | A61M 15/0065 |
| | | | 128/203.15 |
| 2006/0096594 A1* | 5/2006 | Bonney | A61M 15/0065 |
| | | | 128/202.17 |
| 2009/0090787 A1* | 4/2009 | Crosby | G06M 1/166 |
| | | | 235/91 R |
| 2009/0139516 A1* | 6/2009 | Augustyn | A61M 15/0045 |
| | | | 128/200.23 |
| 2010/0229857 A1* | 9/2010 | Von Schuckmann | |
| | | | A61M 15/009 |
| | | | 128/200.23 |
| 2011/0253138 A1* | 10/2011 | Briant | A61M 15/0045 |
| | | | 128/203.12 |
| 2011/0259324 A1* | 10/2011 | Hochrainer | A61M 15/009 |
| | | | 128/200.14 |
| 2014/0053838 A1* | 2/2014 | Berenshteyn | A61M 15/0065 |
| | | | 128/203.15 |
| 2014/0352692 A1* | 12/2014 | Mayer | G06M 1/04 |
| | | | 128/203.12 |

FOREIGN PATENT DOCUMENTS

| | | | | |
|---|---|---|---|---|
| FR | 2 858 867 A1 | 2/2005 | | |
| WO | WO-9828033 A2 * | 7/1998 | .......... | A61M 15/009 |
| WO | 2006/051073 A1 | 5/2006 | | |
| WO | WO-2006062448 A1 * | 6/2006 | .......... | A61M 15/009 |
| WO | 2007/045904 A1 | 4/2007 | | |
| WO | 2007/124406 A2 | 11/2007 | | |
| WO | WO-2009086009 A1 * | 7/2009 | ........ | A61M 15/0065 |
| WO | WO-2010135253 A2 * | 11/2010 | ........ | A61M 15/0045 |

* cited by examiner

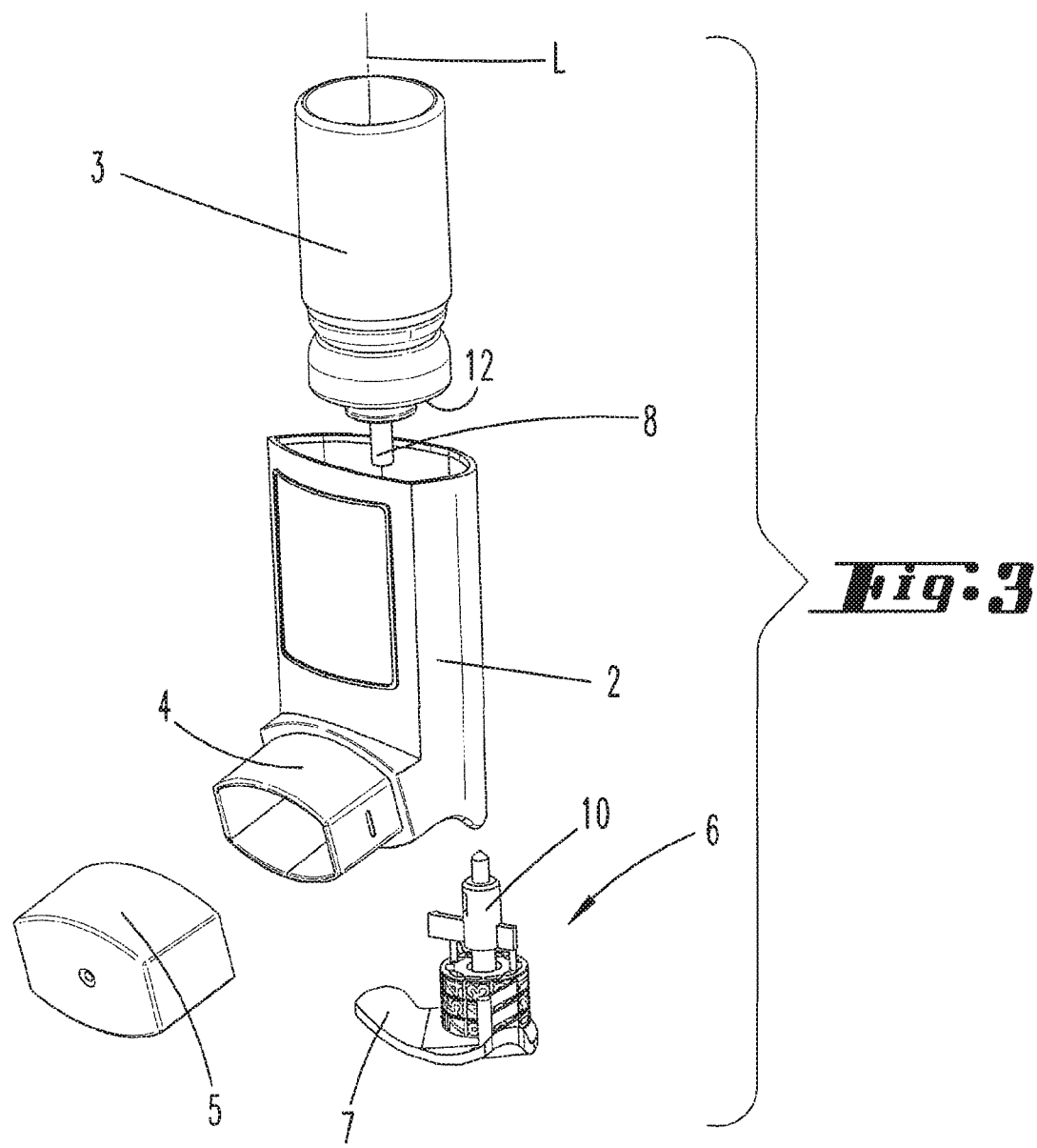

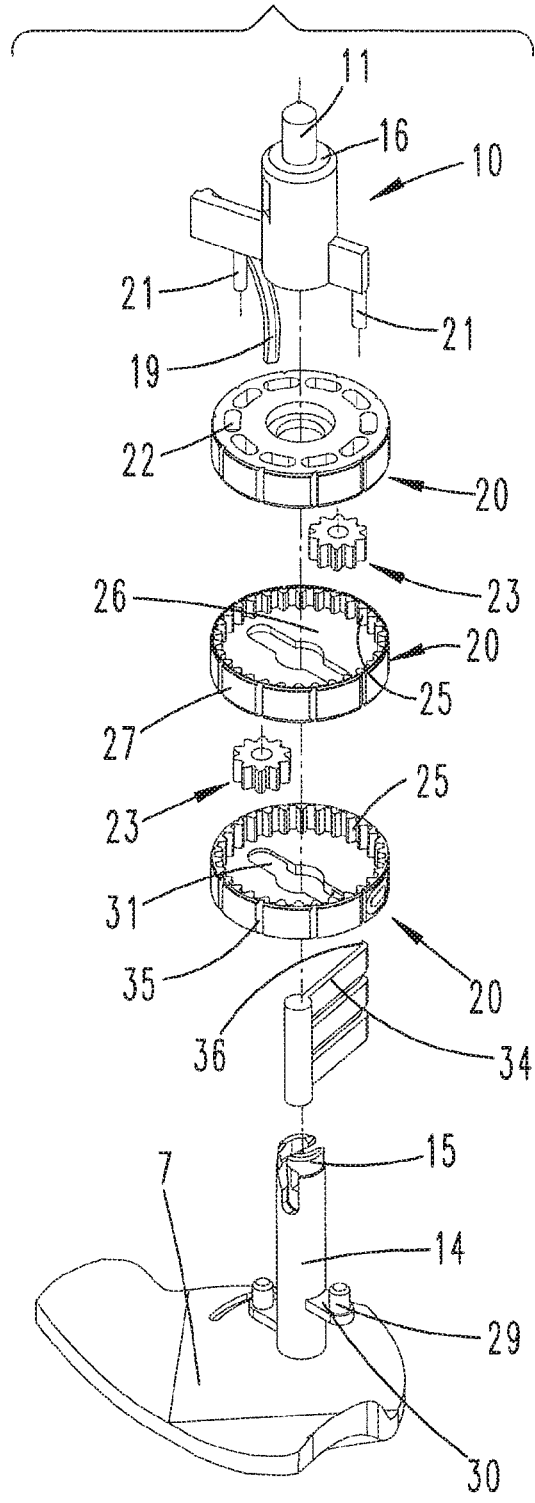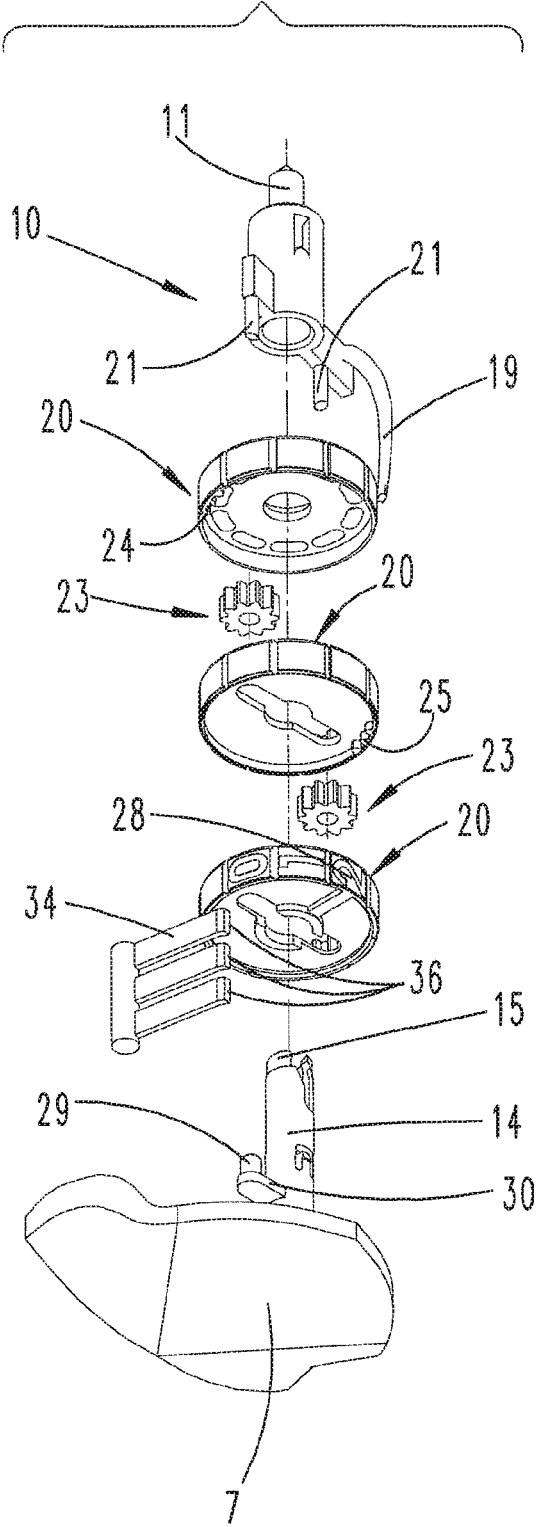

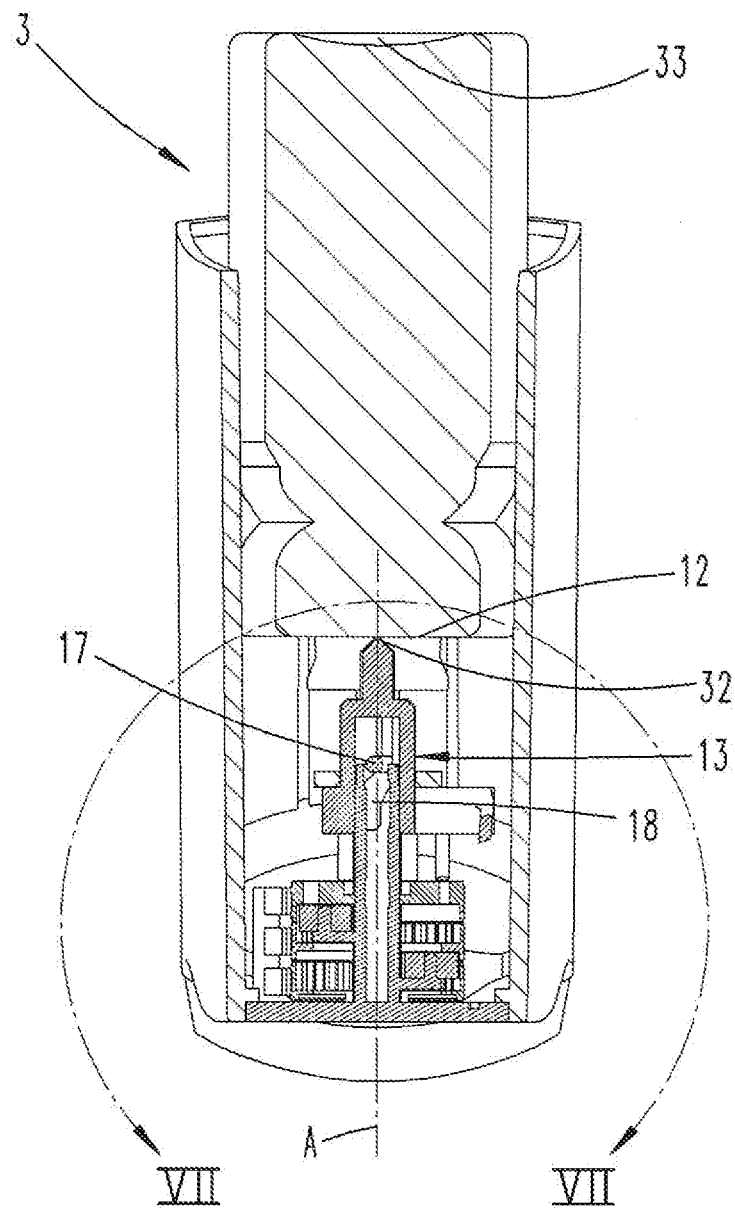

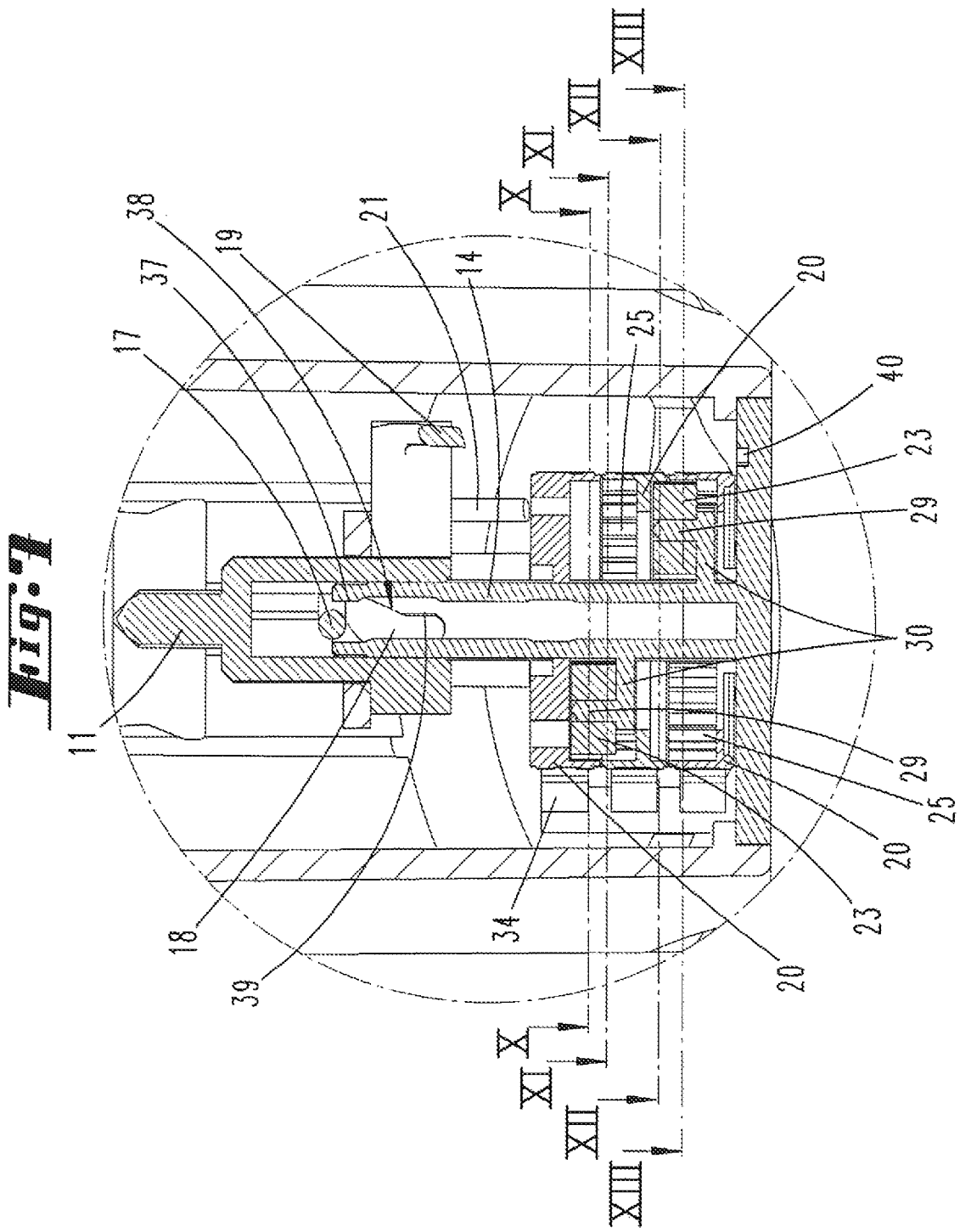

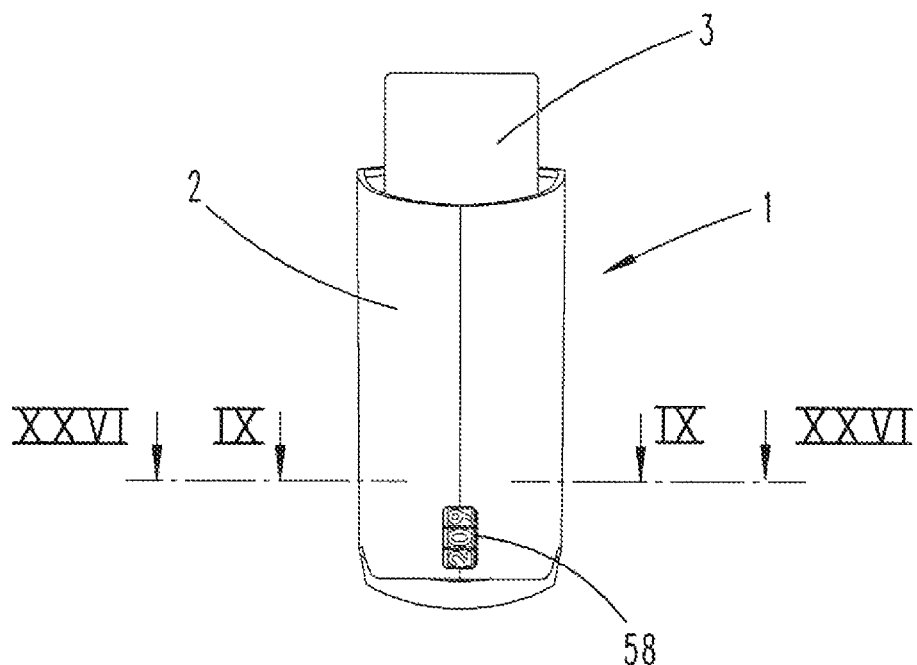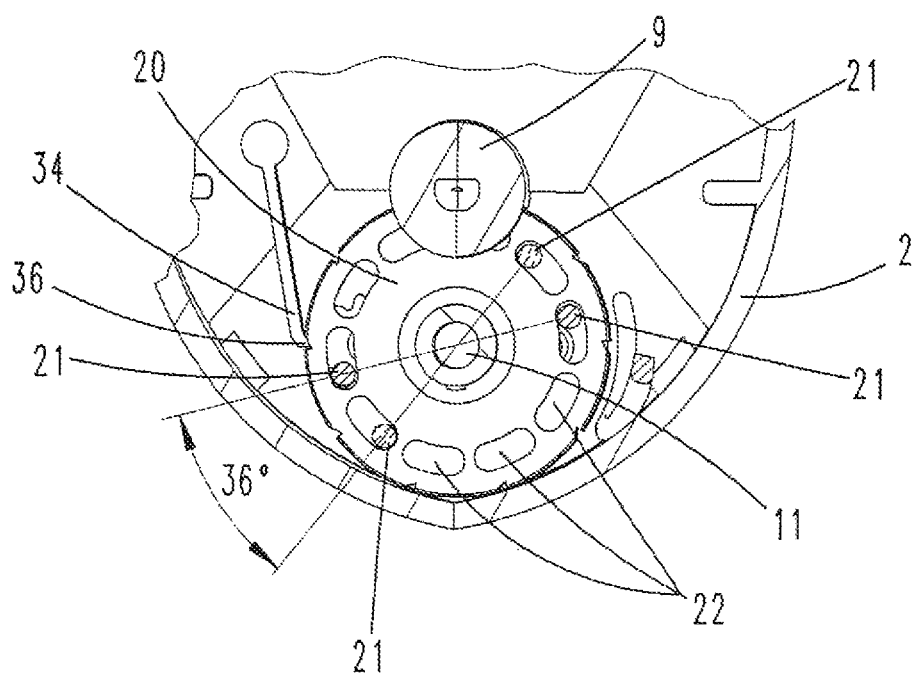

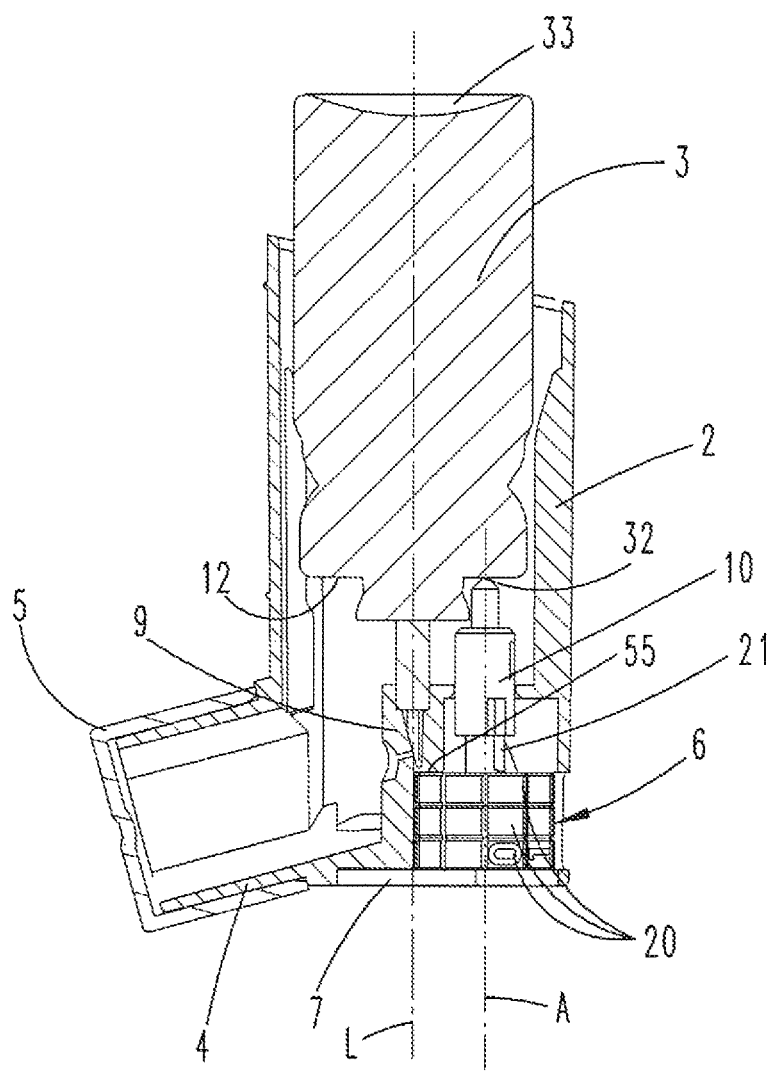

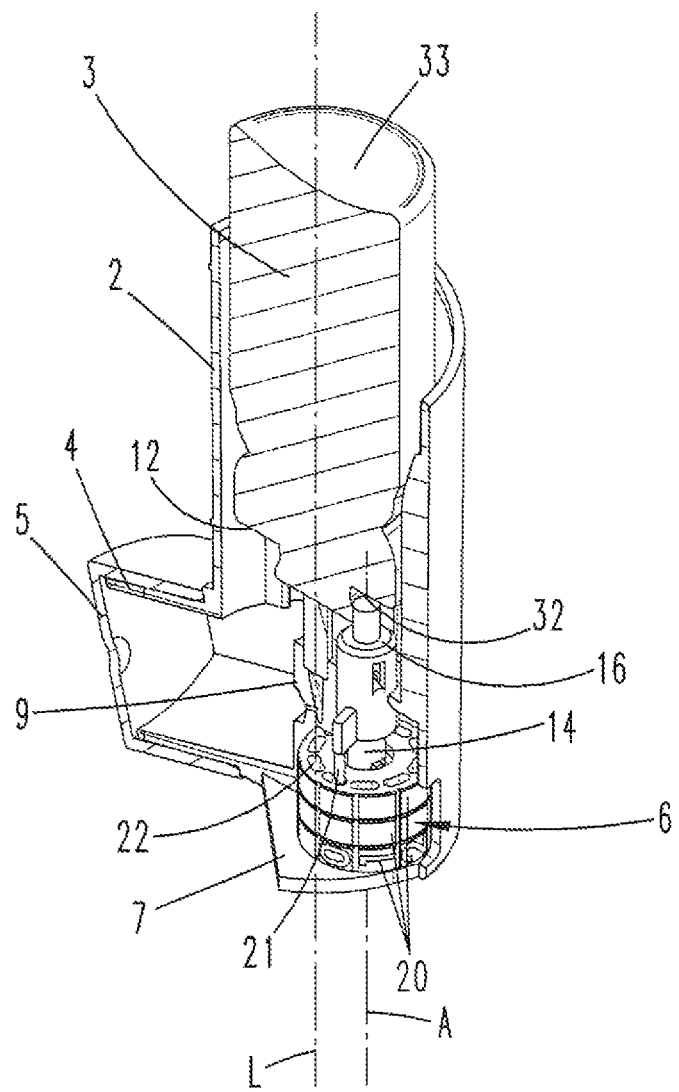

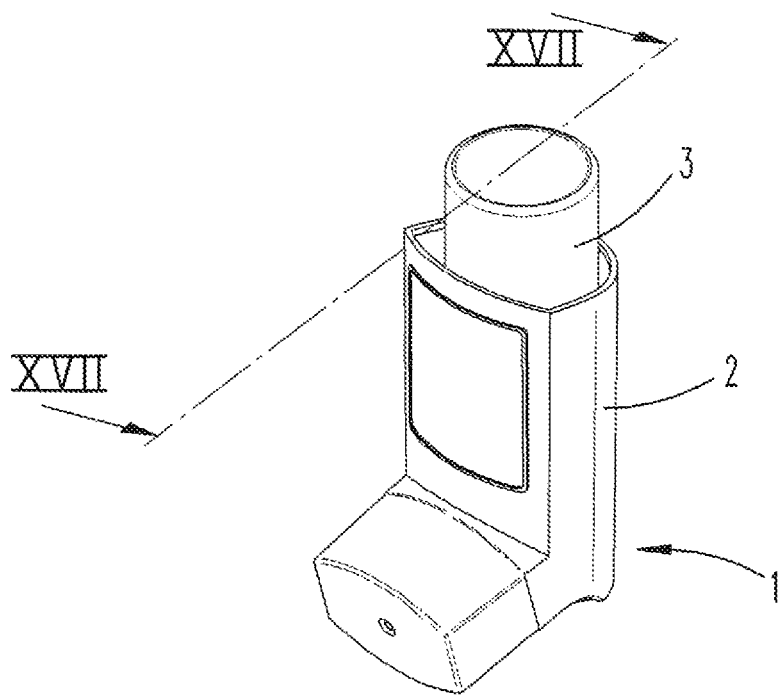
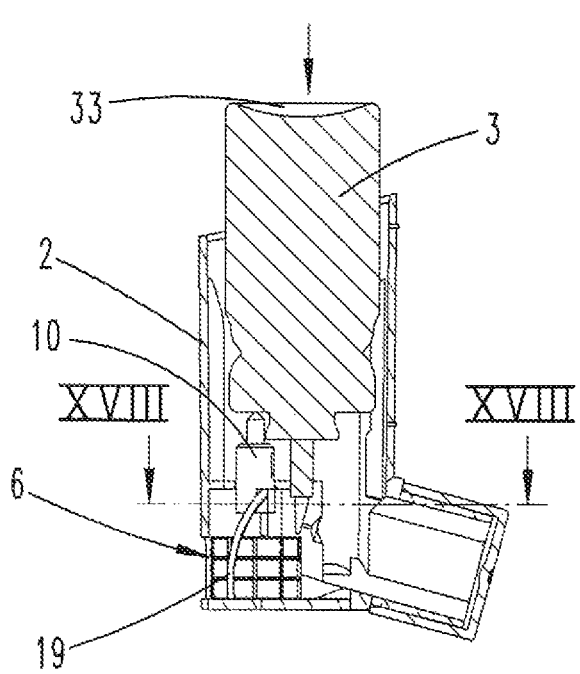
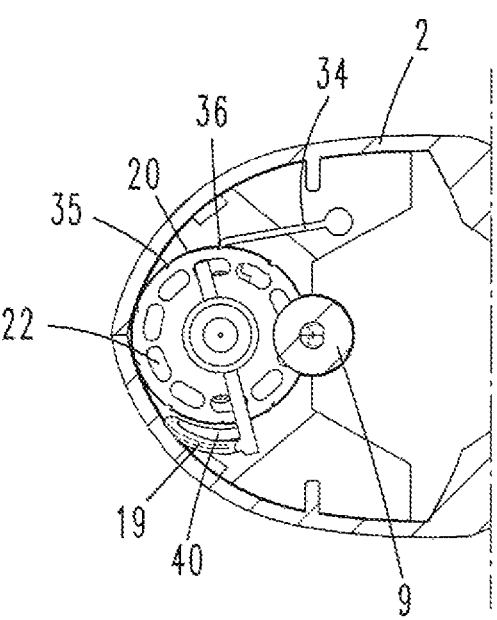

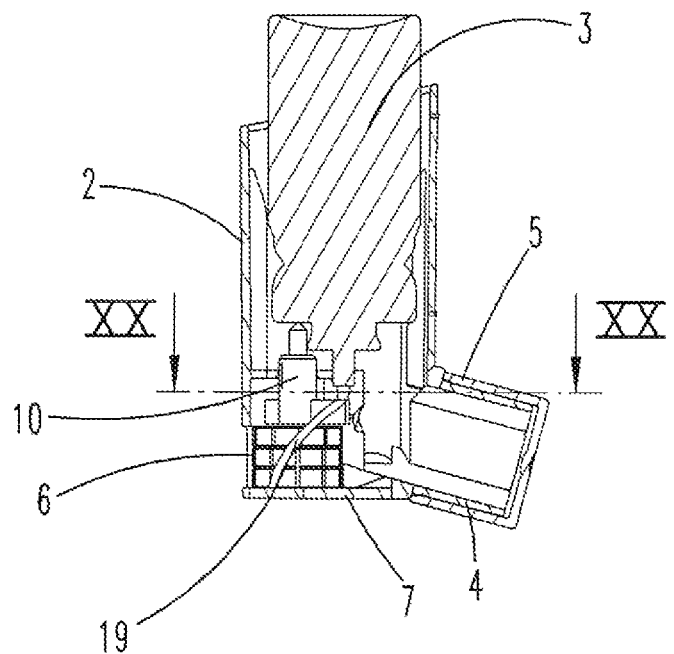
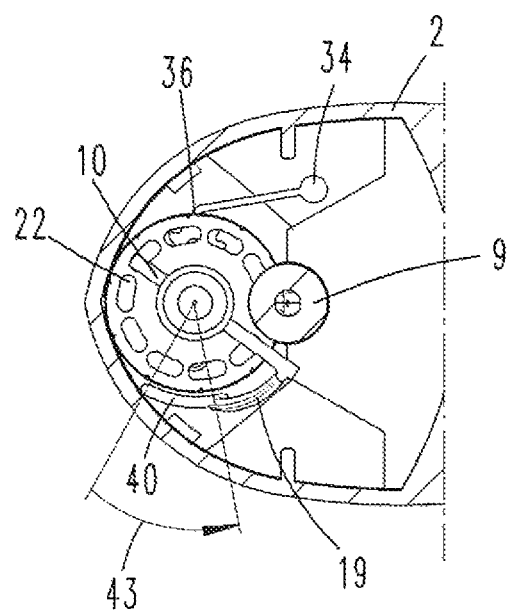

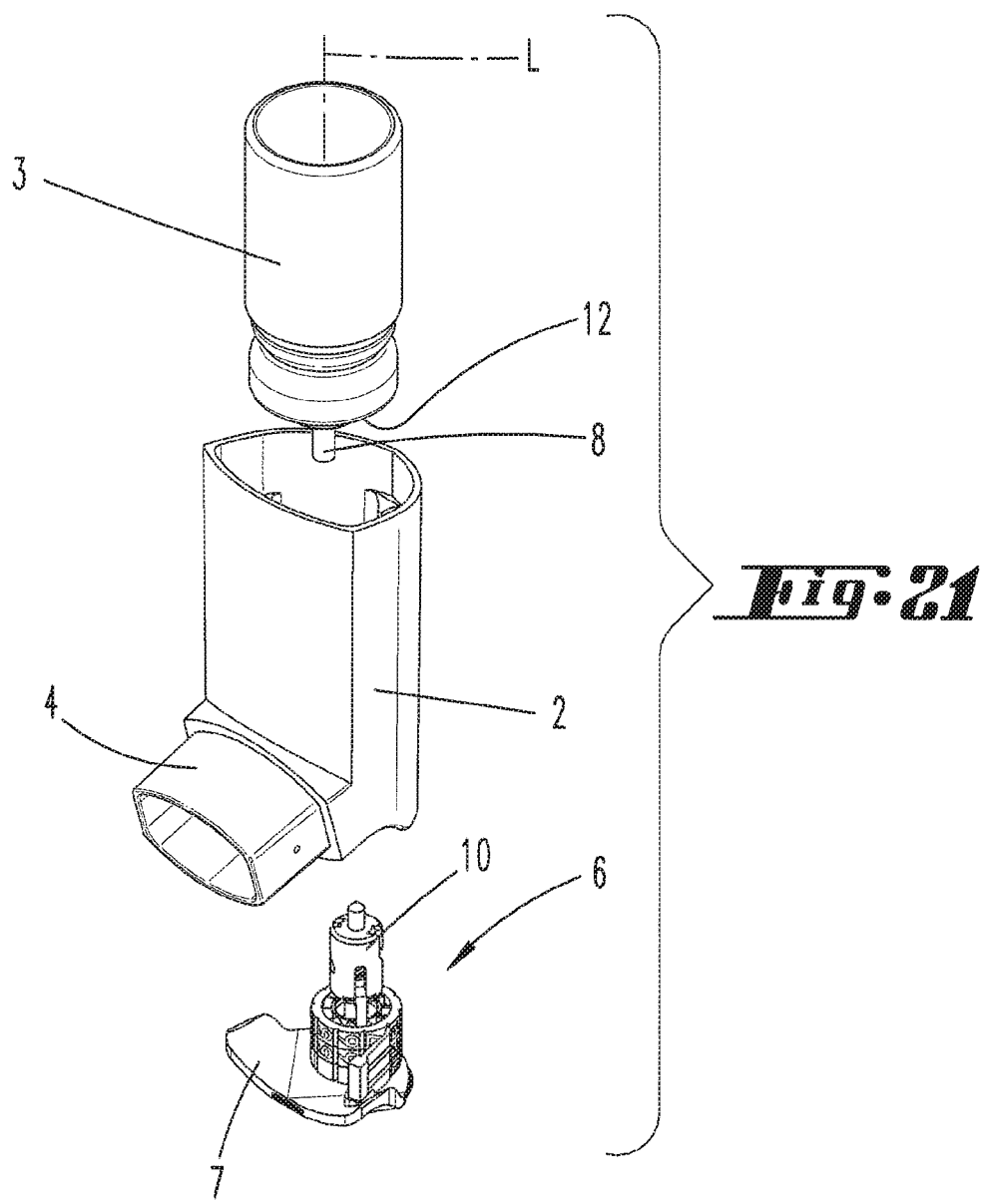

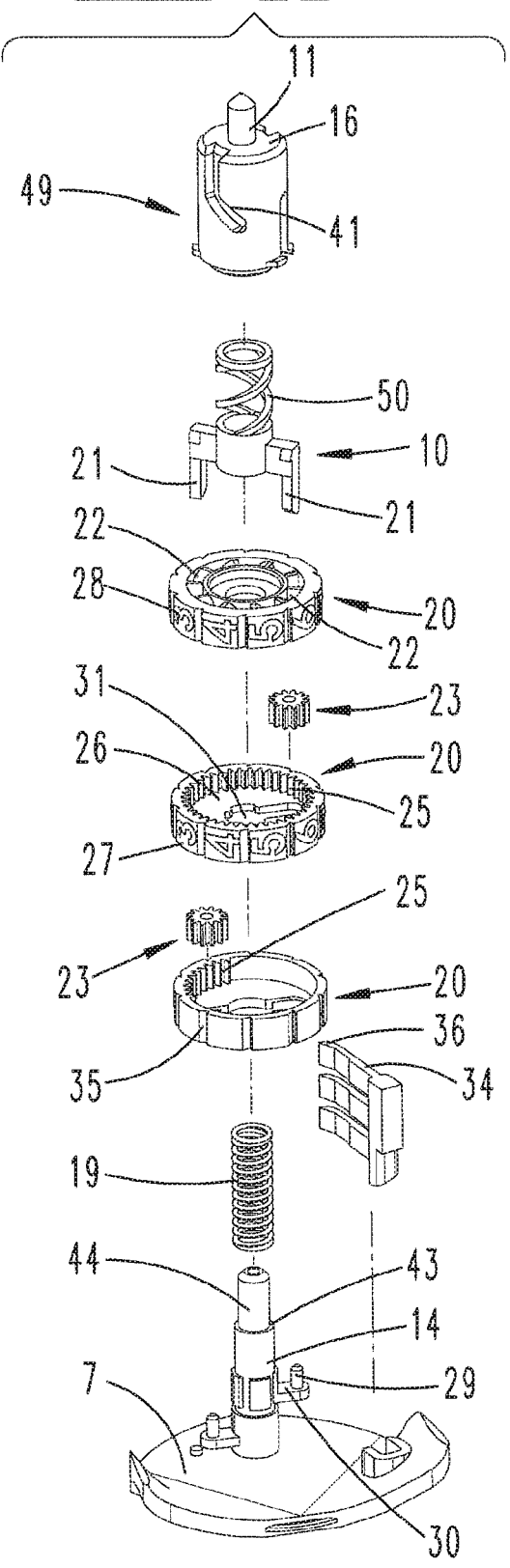
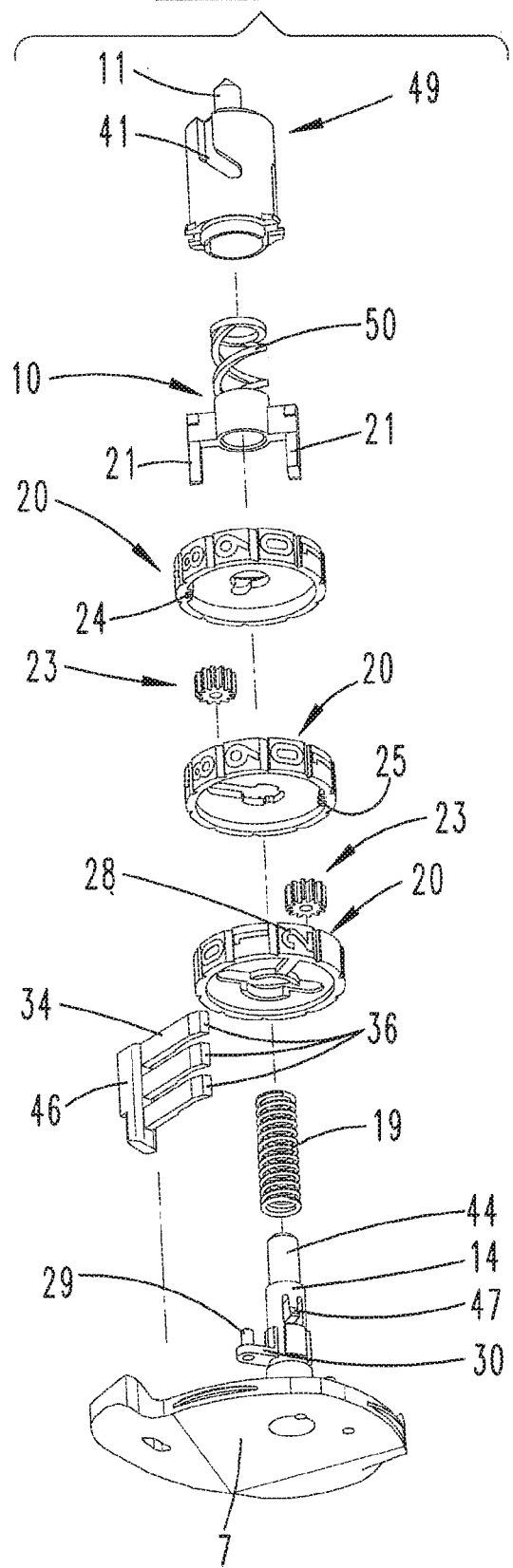

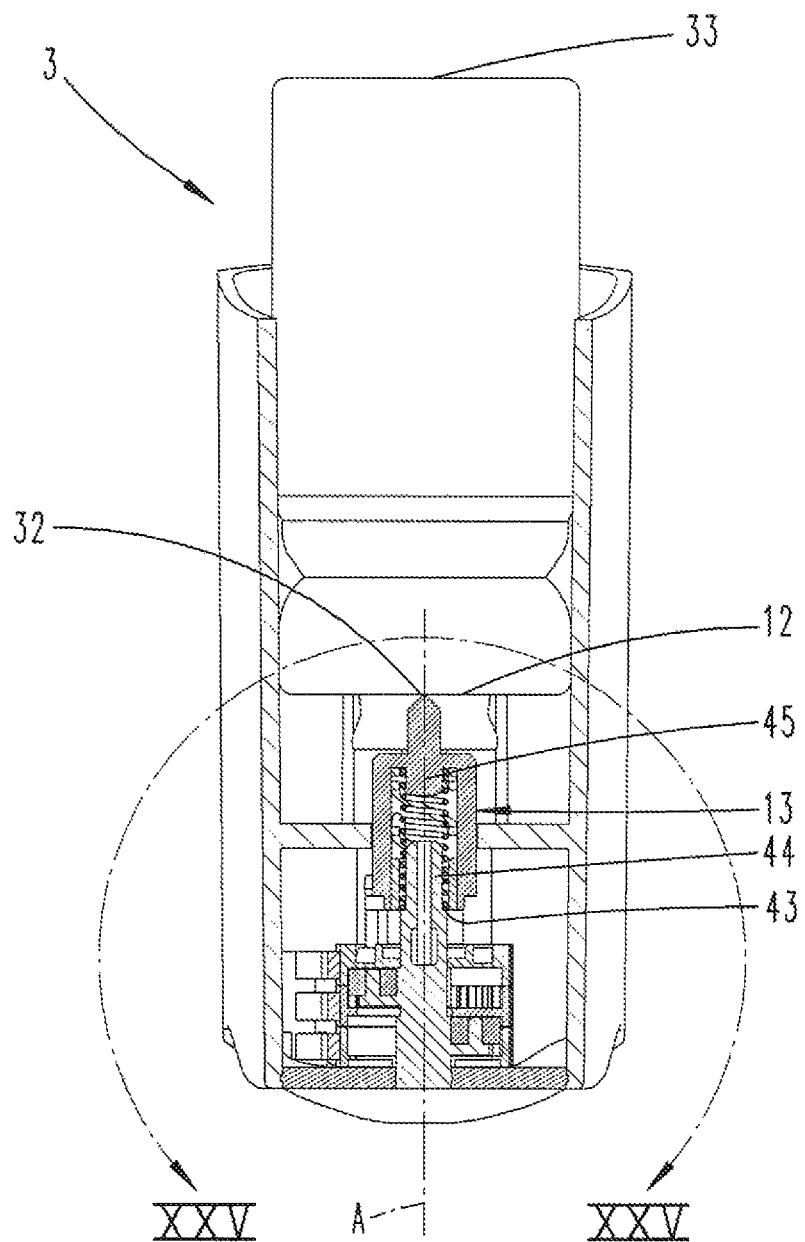

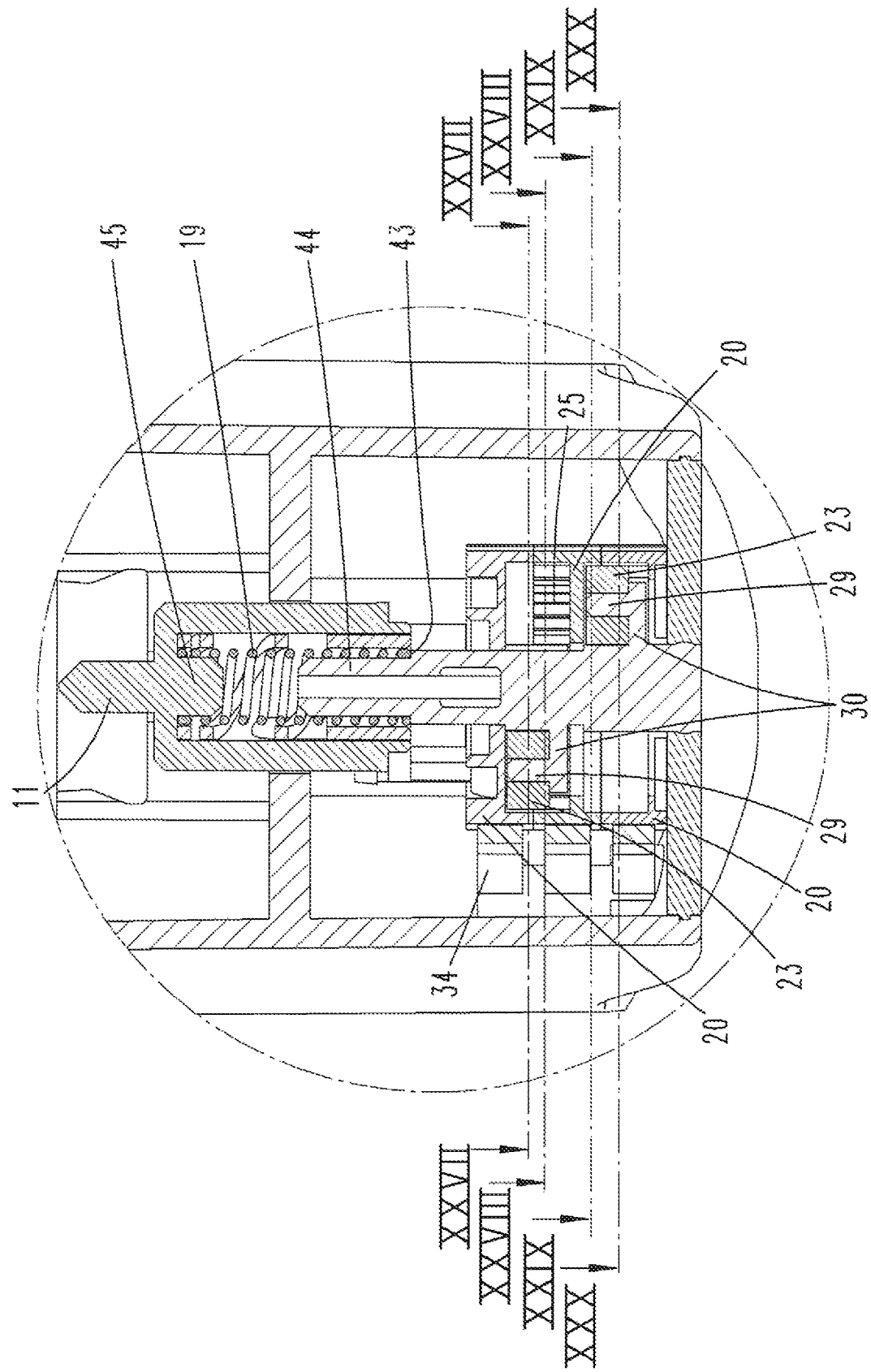

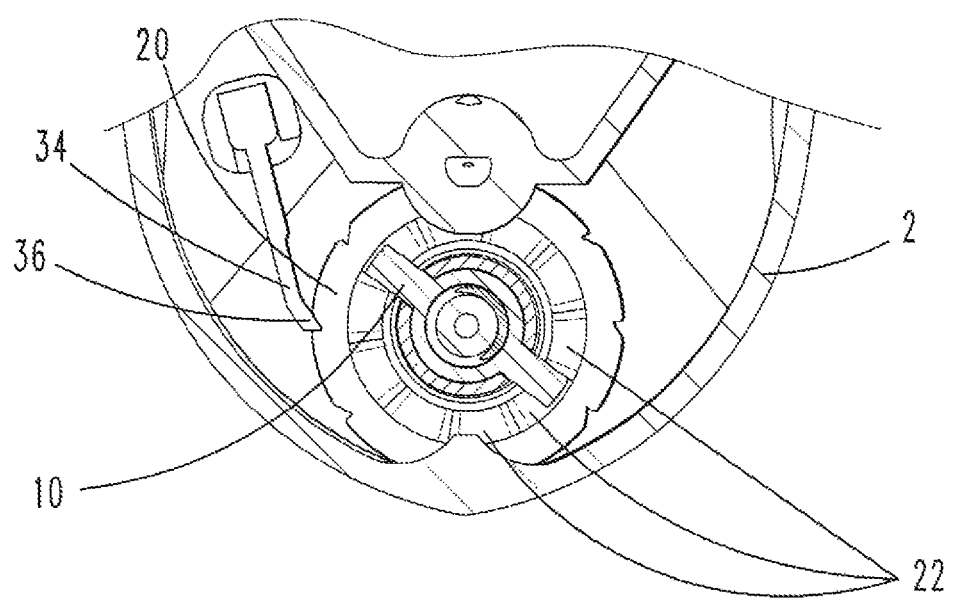

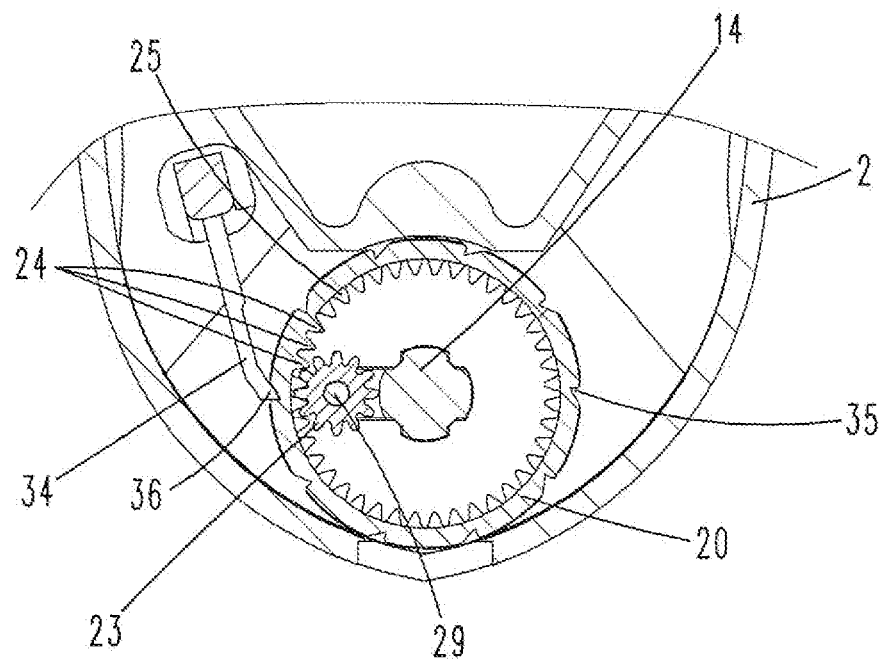
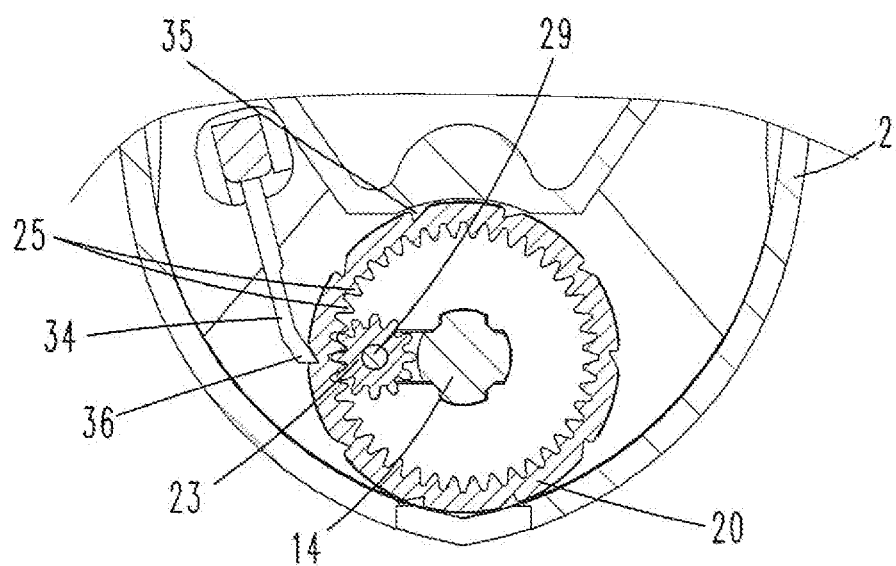

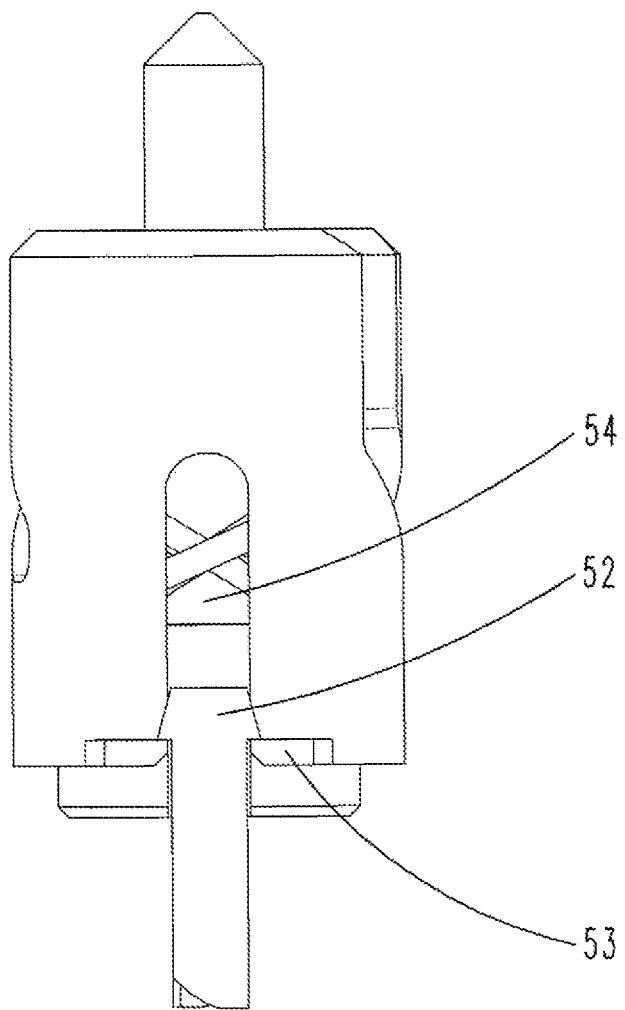

COUNTER AND HANDHELD DEVICE WITH COUNTER

CROSS REFERENCE TO RELATED APPLICATIONS

This application is the National Stage of PCT/EP2014/071427 filed on Oct. 7, 2014, which claims priority under 35 U.S.C. § 119 of German Application Nos. 10 2013 111 381.8 filed on Oct. 15, 2013 and 10 2014 114 462.7 filed on Oct. 6, 2014, the disclosures of which are incorporated by reference. The international application under PCT article 21(2) was not published in English.

The invention firstly pertains to a counter for a handheld device for dispensing pharmaceutical substances.

The invention furthermore pertains to a handheld device with such a counter.

Counters of this type have already been disclosed in different variations. In this context, we refer, for example, to WO 2006/051073 A1 (U.S. Pat. No. 7,448,342 B2, U.S. Pat. No. 7,827,984 B2). We furthermore refer, e.g., to WO 2007/045904 A1.

In a counter known from U.S. Pat. No. 6,283,365 B1, the drive part is realized as part of the stationary rotational axis. The drive part is specifically composed of two pieces, wherein the counter wheel cooperates during an overall stroke with different regions of the drive part, namely on a forward path and on a return path. The acting part directly displaces the counter wheel, which is visible through a window in the acting part and remains rotatable in frictional contact with the acting part.

In a counter known from WO 2007/124406 A2, the drive part can be moved by means of angular faces that are designed for cooperating with corresponding angular faces on the acting part. The acting part merely carries out a reciprocating motion in the direction of the rotational axis. A required rotational motion of the drive part is realized due to the cooperation between the angular faces of the drive part and of the acting part only.

In a counter and a handheld device with counter known from DE 10061723 A1, a shifting element is provided and acted upon by an acting part that can only be axially moved relative thereto, namely an actuating button or a spray nozzle. The rotation is realized about a merely geometric rotational axis by means of an external guide.

In the initially mentioned counter and handheld device with counter of the type disclosed in WO 2006/051073 A1, the counter wheel is turned by a planet wheel, which in turn is seated on a sun wheel that is geared on its underside. The sun wheel is acted upon by an incremental shifting finger. If the sun wheel is considered to be a drive part, it merely rotates about a geometric rotational axis.

Based on the latter prior art, the invention aims to disclose a well functioning and easily designed counter and a handheld device with such a counter.

This objective is firstly attained with a counter according to one aspect of the invention, in which it is proposed that the acting part is rotationally moved and connected to the drive part in order to rotate jointly therewith, and that the drive part features a guide section, by means of which it is seated on the first rotational axis of the counter realized in the form of a stationary pin in the assembled state of the counter.

The above-defined objective is also attained with a handheld device with a counter according to another aspect of the invention, in which it is proposed that the counter features a bottom part that forms part of the housing and is inserted therein, wherein the bottom part at least partially overlaps the substance container in the direction of the longitudinal axis thereof, and that the bottom part carries a stationary first rotational axis for the counter wheel, on which the drive part is preferably also guided, wherein the drive part is located on the side of the substance container referred to the counter wheel.

The drive part and the acting part may be realized in one piece. They may also be realized in the form of parts that can be moved relative to one another, but are coupled in the rotating direction. In a one-piece design, they may particularly be integrally molded of the same material, for example, in the form of an integral injection-molded plastic part.

The acting part preferably serves for transmitting a motion of a substance container, in which the pharmaceutical substance is accommodated, to the drive part, particularly during a dispensing actuation of the substance container. It is essential that a rotational motion of the drive part take place. An axial motion of the drive part would furthermore be conceivable, but is not absolutely imperative. When a rotational motion is generated by acting upon the acting part, it is also directly transmitted to the drive part if the acting part and the drive part consist of separate parts.

The rotational motion of the acting part and of the drive part is preferably a reciprocating rotational motion. The drive part respectively participates in the reciprocating motion if it is not realized in one piece with the acting part anyway. The acting part and/or the drive part preferably always rotate within the handheld device by the same predefined angle starting from practically the same starting position.

The rotational coupling between the acting part and the drive part, particularly in a rigidly connected or integral design of the acting part and the drive part, accordingly also results in a rotation of the acting part relative to the substance container during an actuation. In this respect, it would basically be possible that the region of the jointly rotating and interconnected acting and drive parts, which cooperates with the substance container, is rotatable, but rigidly connected to the region that forms the drive part or acts upon the drive part in the direction of the rotational axis. In this case, a rotation between the substance container and the acting part does not necessarily take place. However, direct rotational friction between the substance container and the acting part may also occur during a dispensing actuation of the substance container and a corresponding rotation of the acting part, particularly if no such specifically rotatable region is provided.

The rotational motion of the acting part is preferably superimposed with a motion in the direction of the rotational axis. Consequently, the rotational motion of the acting part takes place simultaneously with a motion in the direction of the rotational axis when the substance container is acted upon accordingly.

It is furthermore preferred that the drive part and/or the acting part feature a shaped engagement section that is engaged or engages with an engagement opening and/or an engagement face of the counter wheel during the course of a corresponding displacement of the acting part or the drive part, wherein said engagement face may, if necessary, be realized in the form of a boundary of the engagement opening. Accordingly, the drive part—if applicable, in the form of a corresponding region of the acting part—and the counter wheel are constantly engaged with one another or not constantly engaged with one another.

The rotational axis, about which the drive part and therefore also the acting part are rotatable, is preferably stationary with respect to a housing, into which the counter is inserted.

The drive part may not only feature a shaped engagement section for cooperating with the counter wheel, but also a shaped gear section. The shaped gear section makes it possible to separately act upon the drive part or the combined acting and drive part in order to realize its rotation. If the cooperation between the drive part and the counter wheel results in a rotation of the counter wheel, this cooperation takes place during a relative motion between the drive part and the counter wheel in the direction of the rotational axis.

Whenever the preceding and following description refers to the drive part, this reference concerns the corresponding region of the combined acting and drive part. In the preferred one-piece design, it accordingly also concerns the combined part as a whole.

It is preferred to arrange the drive part coaxial to the rotational axis.

The drive part may be completely separated from the counter wheel prior to a displacement such that it does not contact the counter wheel. Nevertheless, an overlap between the drive part and the counter wheel may still exist in a horizontal plane extending perpendicular to the rotational axis. Such an overlap preferably only exists between a downwardly protruding shaped engagement section of the drive part and a boundary of the engagement opening, particularly the aforementioned engagement face. However, it would also be conceivable that no horizontal plane, in which the drive part and the counter wheel overlap one another, is defined prior to a displacement.

It is also preferred to capture the drive part on the first rotational axis prior to a displacement. This connection may be produced, for example, by means of a spring that acts between the drive part and the rotational axis. The spring may consist of a return spring that acts upon the drive part in the direction of the position prior to the displacement.

The first rotational axis may be realized similar to a pin with a free upper end. The rotational axis may feature a projection that is realized, e.g., in the form of a circumferential shoulder, on which the return spring can be seated.

The shaped gear section of the drive part and/or the acting part may consist of a slotted link. It may also consist of a slide block. It may furthermore consist of a geared segment.

The gear part cooperating with the shaped gear section may be realized outside the actual counter, for example, in a housing of the handheld device, into which the counter is inserted.

The gear part may alternatively also be realized on a region of the counter, particularly of the stationary rotational axis. The gear part can be respectively adapted to the shaped gear section provided. For example, the gear part may consist of a slide block if the shaped gear section is realized in the form of a slotted link. Accordingly, the gear part may consist of a slotted link if the shaped gear section is realized in the form of a slide block. If the shaped gear section is realized in the form of a geared segment, the gear part accordingly consists of another geared segment that is designed for meshing with the geared segment of the shaped gear section.

It is furthermore preferred that the counter comprises part of the housing of the handheld device. Accordingly, the handheld device, into which the counter is inserted, is missing part of its housing in this case. This missing part is only supplemented when the counter is inserted into the handheld device in order to thereby complete the housing.

One or more springs acting upon the drive part, for example two springs, can also be supported on the inner side of the aforementioned part of the housing, which in this embodiment forms part of the counter, preferably as an alternative, but if necessary also in combination with a support on the rotational axis. A rigid connection between the rotational axis and the housing may particularly consist of an integral material connection. In any case, the rigid connection is preferably realized in such a way that no relative motion is possible between the aforementioned part of the housing and the rotational axis.

One or two springs or, if necessary, even more springs may extend laterally of the counter wheel and in the direction of the first rotational axis such that they overlap the counter wheel. If two springs are provided for cooperating with the drive part, these springs may extend opposite to one another referred to the first rotational axis.

With respect to the spring action, it would also be conceivable that one spring acts directly between the acting part and the rotational axis and an additional spring acts between the drive part and the acting part. In this case, the latter spring is provided, in particular, for allowing a motion between the drive part and the acting part in the direction of the rotational axis, wherein this type of motion preferably can also be realized independently of such a spring.

The drive part may be captured on the acting part movably in the direction of the rotational axis, but practically immovably in the rotating direction. It may particularly be snap-fitted thereon.

In a preferred embodiment, the rotation of the drive part is realized due to the aforementioned cooperation between the shaped gear section and the gear part only.

It is furthermore preferred to provide several counter wheels. These counter wheels may be arranged, in particular, coaxial to one another. The counter wheels may furthermore be arranged coaxial to the rotational axis and/or on top of one another in the direction of the rotational axis. In this case, a cooperation between a shaped engagement section and an engagement opening is preferably only realized on one counter wheel, particularly only on the counter wheel that is directly assigned to the drive part (and typically forms the uppermost counter wheel).

The drive part may feature a shaped engagement section in the form of an engagement pin. The engagement pin may extend axially parallel to the rotational axis.

One counter wheel, preferably the counter wheel that is directly assigned to the drive part, may feature one or more engagement openings. An engagement opening may be designed and arranged for receiving the engagement pin.

An engagement opening is preferably realized with an engagement face. The engagement face may extend in a curved or oblique fashion referred to a vertical line such that a motion of the shaped engagement section, e.g. the engagement pin, if provided, in the direction of the rotational axis results in a circumferential motion of the counter wheel about the rotational axis, i.e. a rotational motion. Due to a corresponding design of the engagement face, this rotational motion is preferably superimposed with the rotational motion resulting from the cooperation of the drive part with the housing by means of the shaped gear section.

A transmission gearwheel may be provided between two counter wheels that are arranged directly adjacent to one another in the direction of the rotational axis. The transmission gearwheel may be rotatable about a second rotational axis. The transmission gearwheel may furthermore extend transverse to its second rotational axis such that it overlaps both counter wheels. The upper counter wheel is geared in a certain circumferential region only such that the lower counter wheel is only rotated with the aid of the transmission gearwheel if this certain geared region engages with the transmission gearwheel due to a prior rotation of the lower counter wheel.

The transmission gearwheel may be rotatably held on a radial arm of the first rotational axis. The radial arm may form the second rotational axis.

Two transmission gearwheels may particularly be provided. In this context, it is also preferred to provide two radial arms. The two radial arms may furthermore also be spaced apart in the direction of the first rotational axis in this case.

One, several or all counter wheels may cooperate with a reverse lock. A reverse lock may be realized in the form of a locking part that acts upon an outer circumferential surface of a counter wheel featuring the characters. A locking part may be realized in the form of a spring-loaded lever part. It may feature a free end region that can be freely moved by the spring and preferably is engaged with the respective counter wheel, as well as a mounting end region that is preferably realized integrally with a mounting of the lever part on the housing.

A preferred locking part is realized in a finger-like fashion and extends transverse to the direction of the first rotational axis.

The locking part may be fixed on the aforementioned part of the housing, which forms part of the counter in this case. It may act based on elastic deformation only.

The invention also pertains to a handheld device for dispensing pharmaceutical substances, particularly an inhalation medication, with a housing, wherein a substance container with a longitudinal axis, which is actuated by means of a dispensing stroke, and a counter are accommodated in the housing, and wherein the counter comprises at least one counter wheel that features legible characters, as well as a drive part that rotationally acts upon the counter wheel and is displaced during a dispensing stroke of the substance container.

In this respect, we also refer to the initially cited prior art.

In order to advantageously design a handheld device, particularly a handheld device with the above-described characteristics, it is proposed that the counter features a bottom part, which may form part of the housing and can be inserted therein, wherein the bottom part at least partially overlaps the substance container in the direction of its longitudinal axis and carries a stationary first rotational axis for the counter wheel, on which the drive part is also arranged, and wherein the drive part is viewed from the bottom part located on the side of the substance container referred to the counter wheel.

The bottom part may form an integral part of the housing, but not be integrally connected thereto, such that it forms a section of the outer surface of the housing in the inserted state. It preferably forms a section of the outer surface of the housing in a bottom region thereof. A bottom region of the housing is the lower region in the direction of the substance container, which also features the receptacle for a dispensing projection of the substance container.

Another advantage of a handheld device of the above-described type is achieved in that the drive part and/or an acting part acting upon the drive part features a shaped gear section for cooperating with a stationary gear part of the housing in order to thereby realize a rotational motion of the drive part relative to the housing during the course of a displacement.

With respect to the counter, the handheld device may furthermore feature one or more of the additional characteristics described above with reference to the counter.

Such a handheld device is designed, in particular, for dispensing sprayable substances. With respect to examples of such substances, we refer to the substances mentioned in the initially cited publications.

The invention is described in greater detail below with reference to the attached drawings which, however, merely show an exemplary embodiment. In these drawings:

FIG. 3 shows a first exploded view of the handheld device, the substance container and the counter according to a first embodiment;

FIG. 4 shows a second exploded view of the counter according to the first embodiment only, namely in the form of a oblique top view;

FIG. 5 shows an illustration according to FIG. 4 in the form of an oblique bottom view;

FIG. 6 shows a cross section through the handheld device along the line VI-VI in FIG. 2;

FIG. 7 shows an enlarged detail of the region VII-VII in FIG. 6;

FIG. 8 shows a rear view of the handheld device according to the first and second embodiment;

FIG. 9 shows a cross section through the object according to the first embodiment in FIG. 8 along the line IX-IX;

FIG. 14 shows a schematic sectioned side view of the handheld device according to the first embodiment with a counter arranged therein;

FIG. 15 shows a perspective view according to FIG. 14 in the form of an oblique top view;

FIG. 16 shows another illustration according to FIG. 1 in order to elucidate an additional plane of section;

FIG. 17 shows a section through the object according to FIG. 16 along the line XVII-XVII;

FIG. 18 shows a cross section through the object according to FIG. 16 and FIG. 17 in the plane XVIII-XVIII in FIG. 17;

FIG. 19 shows an illustration according to FIG. 17 in the pressed-down state of the substance container;

FIG. 20 shows a cross section through the object according to FIG. 19 in the plane XX-XX;

FIG. 21 shows an illustration according to FIG. 3 of an additional embodiment;

FIG. 22 shows an illustration according to FIG. 4 of the additional embodiment;

FIG. 23 shows an illustration according to FIG. 5 of the additional embodiment:

FIG. 24 shows a cross section through the additional embodiment along the line XXIV-XXIV in FIG. 2;

FIG. 25 shows an enlarged detail of the region XXV-XXV in FIG. 24;

FIG. 26 shows a cross section through the object according to FIG. 8, which is realized in accordance with the additional embodiment, along the line XXVI-XXVI;

FIG. 27 shows a cross section through the object according to FIG. 25 along the line XXVII-XXVII;

FIG. 28 shows a cross section through the object according to FIG. 25 along the line XXVIII-XXVIII;

FIG. 35 shows a side view of the drive part connected to the acting part.

A handheld device 1 for dispensing sprayable substances, particularly inhalation medications, is initially described below with reference to FIGS. 1-3.

The handheld device 1, which is also referred to as an inhaler, features a housing 2 and a substance container 3 removably accommodated therein. The substance container 3 is also referred to as a cartridge or canister.

Figure 1:
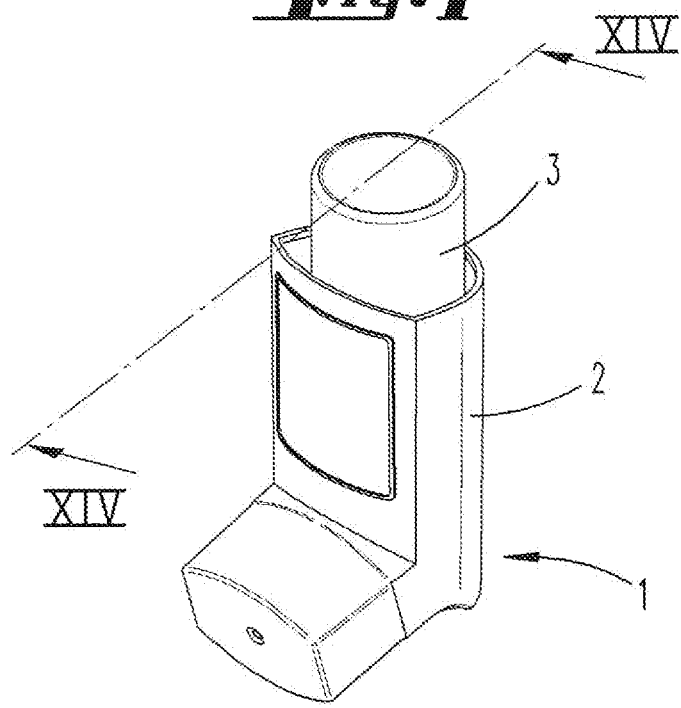
FIG. 1 shows a first embodiment of a handheld device for dispensing sprayable substances in the form of an oblique front view.
Figure 2:
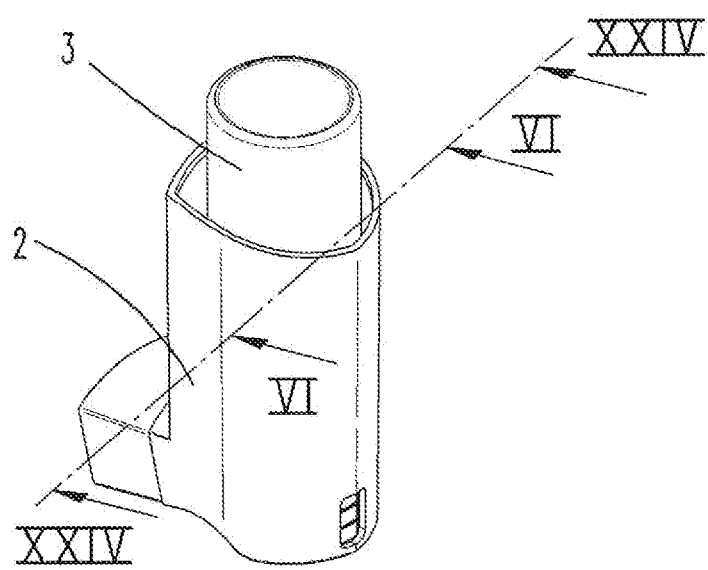
FIG. 2 shows the handheld device according to FIG. 1 in the form of an oblique rear view.

On the handheld device 1 illustrated in FIGS. 1 and 2, a dispensing nozzle 4 (FIG. 3), which the user usually has to put in the mouth and therefore is also referred to as mouthpiece, is covered by a protective cap 5.

A counter 6 is accommodated in the handheld device 1. In the exemplary embodiments, this counter preferably consists of a counter for counting individual doses. Accordingly, a count or a rotational advance of the units counter wheel takes place during each actuation of the device, i.e. during each up-and-down motion of the medication container. The counter 6 preferably features a bottom part 7. According to the exemplary embodiments, the bottom part 7 preferably forms part of the housing 2 and therefore also a corresponding section of the outer surface of the housing. The bottom part 7 is located laterally of the mouthpiece, i.e. the dispensing nozzle 4, in the lower part of the housing 2 that is located laterally adjacent to the mouthpiece.

Another advantage of the design of the counter in combination with a bottom part, which simultaneously forms a supplementary part of the housing, can be seen in that the counter—with the bottom part—can also be inserted into the handheld device when the substance container is already located therein. It can be inserted into the housing 2 in the opposite direction of the substance container.

In the exemplary embodiments, the substance container 3 has to be actuated, in particular manually, in the direction of its longitudinal axis in order to dispense substance. For this purpose, the substance container particularly features a tubular dispensing projection, wherein this dispensing projection has to be conventionally moved in the direction of the interior of the substance container 3 against a spring force in order to dispense substance from the substance container 3. A receptacle 9 (see especially FIG. 14) for the dispensing projection 8 is realized in the housing 2 and deflects the substance dispensed during a dispensing stroke in such a way that it is sprayed into the interior of the dispensing nozzle 4.

The counter 6 and its arrangement in the handheld device 1 are described in greater detail below with reference to FIGS. 4-15.

The counter 6 features a drive part 10 that simultaneously forms its uppermost part because the drive part is combined with the acting part in this exemplary embodiment. During a dispensing stroke, the drive part 10 is acted upon by the substance container 3. It simultaneously functions as an acting part. In the preferred one-piece design of the drive part 10 and the acting part, the acting part also rotates accordingly on the assigned face of the substance container during the course of an actuation. Since the drive part 10 simultaneously functions as an acting part, it features an acting projection 11 that cooperates with a downwardly directed end face 12 of the substance container during a corresponding actuation; see, e.g., FIG. 6.

It is furthermore preferred that the drive part 10 features a guide section 13 (FIG. 6), which is preferably realized in the form of a central guide section in the exemplary embodiment, wherein the drive part is respectively seated on and surrounds the first rotational axis 14 of the counter in the form of a stationary pin in the assembled state of the counter 6. It is preferably seated on the upper side of the first rotational axis 14 and covers an upper end face 15 thereof in a cap-like fashion.

It is accordingly preferred that the guide section 13 is essentially realized in the form of a hollow cylinder. On its upper side, it features an end face 16, from which the acting projection 11 protrudes upward.

A shaped gear section in the form of a slide block 17 is preferably formed on the inner side of the guide section 13 and cooperates with a gear part in the form of a slotted link 18 on the first rotational axis 12. The slotted link 18 essentially extends in the direction of a geometric axis A of the first rotational axis 14. It is particularly preferred that the slide block 17 respectively consists of a pin that traverses a hollow space of the guide section 13 or of a rod section that is anchored in both opposite wall regions of the guide section 13.

It is particularly preferred that the slotted link 18 is divided into three sections. It features a first insertion section 37. The insertion section 37 respectively facilitates or allows a non-rotational motion in the direction of the base of the rotational axis 14 of the drive part 10 in the initial stage of a pressing down the substance container 3. This insertion section is followed by a rotary section 38. In this respect, two opposite slotted link surfaces 39, which appear as angular sections in the cross-sectional illustration according to FIG. 7, are preferably formed such that they extend in opposite directions referred to a top view of the first rotational axis 14.

In other respects, it is also preferred to realize the rotational axis 14 in the form of a hollow cylinder as shown.

Another section 39 of the slotted link ultimately follows the second section 37 in the direction of a bottom of the rotational axis 14. The section 39 once again allows a non-rotational downward motion of the drive part 10 as the substance container 3 is pressed down further.

The drive part 10 is supported on the bottom part 7 by means of a spring 19 in the non-actuated state of the counter or the handheld device. The thusly defined starting position of the drive part 10 is an uppermost position of the drive part 10 referred to the first rotational axis 14.

In this starting position, i.e. in the position of the drive part 10 prior to a displacement for driving a counter wheel 20, the drive part 10 is completely separated from such a (first) counter wheel 20.

The drive part 10 furthermore features a shaped engagement section in the form of an engagement pin or two engagement pins 21 as illustrated in the exemplary embodiment. The engagement pins 21 serve for rotationally driving a counter wheel 20.

It is preferred that the drive part 10 is integrally realized in one piece with the spring 19 and/or the engagement pins 21 and/or the acting projection 11 and/or the guide section 13, e.g. in the form of an injection-molded plastic part.

In the exemplary embodiment, the counter 6 preferably features three counter wheels 20 that are arranged underneath one another. The uppermost counter wheel or the counter wheel directly assigned to the drive part 10 features a row of engagement openings 25 that is distributed over its circumference. A shaped engagement section or an engagement pin 21 can respectively penetrate into an engagement opening 22.

It is preferred to realize the engagement opening 22 in the form of a segment of a circle as shown. It is realized with a certain radius starting from the geometric axis A of the first rotational axis 14. The described design in the form of a segment of a circle is advantageous because the engagement pin 21 still penetrates into the engagement openings 22 during the extension of the engagement pin 21 and a certain associated backward rotation of the drive part 10 relative to the counter wheel 20 that corresponds to a return motion of the engagement pins 21. Several engagement openings 22 are preferably arranged successively in the circumferential direction along a circle with the same radius. For example, ten engagement openings are provided in the exemplary embodiment. It is preferred that two shaped engagement sections of the drive part respectively penetrate into two opposite engagement openings 22 during an actuation.

The engagement opening furthermore features an engagement face, with which the shaped engagement section can come in contact.

Transmission gearwheels 23 are arranged between two counter wheels 20 in the longitudinal direction of the geometric axis A of the first rotational axis 14 such that they overlap these counter wheels.

A transmission gearwheel 23 on the one hand cooperates with first gears 24 of an upper counter wheel 20 referred to the transmission gearwheel 23 (in the conventional operative state of the handheld device) and on the other hand with second gears 25 of a lower counter wheel 20. It can be gathered that the first gears 24 are only realized over part of the circumference of the corresponding counter wheel 20, particularly a small part thereof, whereas the second gears 25 are realized over the entire circumference of the corresponding counter wheel 20.

A counter wheel 20, which forms the central counter wheel of three counter wheels 20 arranged on top of one another as shown, may feature first gears 24 and second gears 25 that, if necessary, are separated by a bottom 26.

The lowermost counter wheel 20 in such an arrangement of three counter wheels on top of one another only has the feature second gears 25.

The first and second gears 24, 25 are preferably realized on an inner surface of a circumferential surface area section 27 of the corresponding counter wheel. It is furthermore preferred to realize the circumferential surface area 27 with the desired number of individually legible characters 28. In this case, a character 28 may be printed on or embossed in the circumferential surface area, produced thereon during the injection-molding process or with a different technique.

A transmission gearwheel 23 is guided on a second rotational axis 29 that preferably is also stationary.

According to the exemplary embodiment, it is furthermore preferred to arrange a second rotational axis 29 on a radial arm 30 of the first rotational axis 14. The radial arm 30 extends radially referred to the geometric axis A of the first rotational axis 14.

A bottom 6 of the counter wheel 20 may feature an opening 31 that is realized similar to a keyhole and not only enables the rotational axis 14 to extend through the counter wheel 20, but also makes it possible to place the counter wheel on the rotational axis 14 such that it overlaps one radial arm or two radial arms 30 as shown in the exemplary embodiment.

The cooperation between the counter wheels 20 and the transmission gearwheels 23, in particular, is described in greater detail below with reference to FIGS. 9-13 that show corresponding cross sections through the counter according to the illustration in FIG. 7.

The cross section in FIG. 9 shows a top view of the uppermost counter wheel 20 with an engagement pin 21 penetrating therein; see FIG. 8. This figure shows both positions of the engagement pin, namely prior to the start of a rotation of the counter wheel 20 and after the completion of a rotation of the counter wheel 20, but prior to the retraction of the engagement pins 21. In the exemplary embodiment, the rotational motion takes place over an angle of 36 degrees as shown. The penetrating engagement pins respectively contact a vertically aligned engagement face during the rotation of the counter wheel 20 in this exemplary embodiment.

Figure 10:
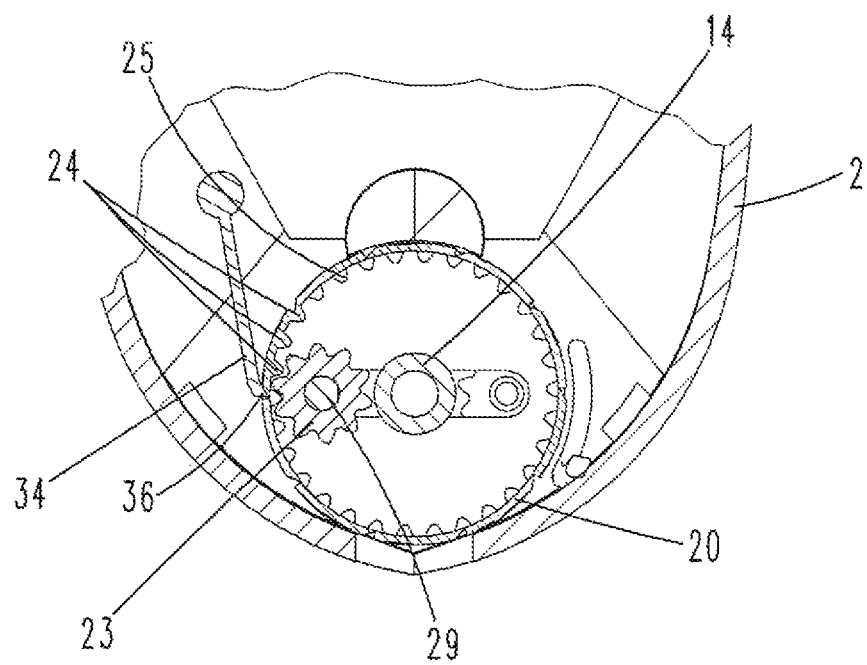
FIG. 10 shows a cross section through the object according to FIG. 7 along the line X-X.

According to the cross-sectional illustration in FIG. 10, the first gears 24, which are only provided over part of the circumference, can cooperate with the first (uppermost) transmission gearwheel 23 (in the corresponding circumferential position of the uppermost counter wheel 20).

Figure 11:
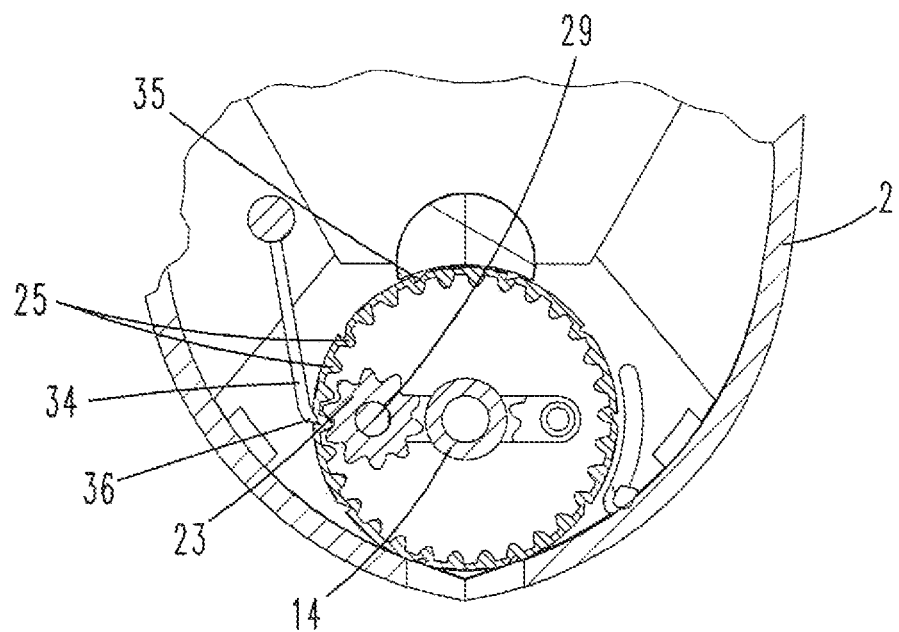
FIG. 11 shows a cross section through the object according to FIG. 7 along the line XI-XI.

The cross-sectional illustration in FIG. 11 shows that the same transmission gearwheel 23 is constantly engaged with the second gears 25 of the additional counter wheel 20 located directly underneath the first counter wheel 20.

Figure 12:
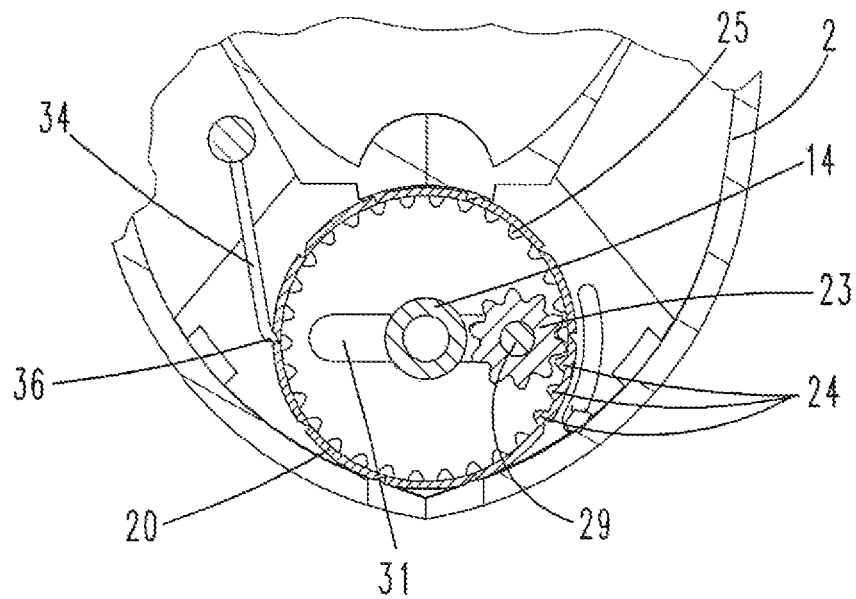
FIG. 12 shows a cross section through the object according to FIG. 7 along the line XII-XII.
Figure 13:
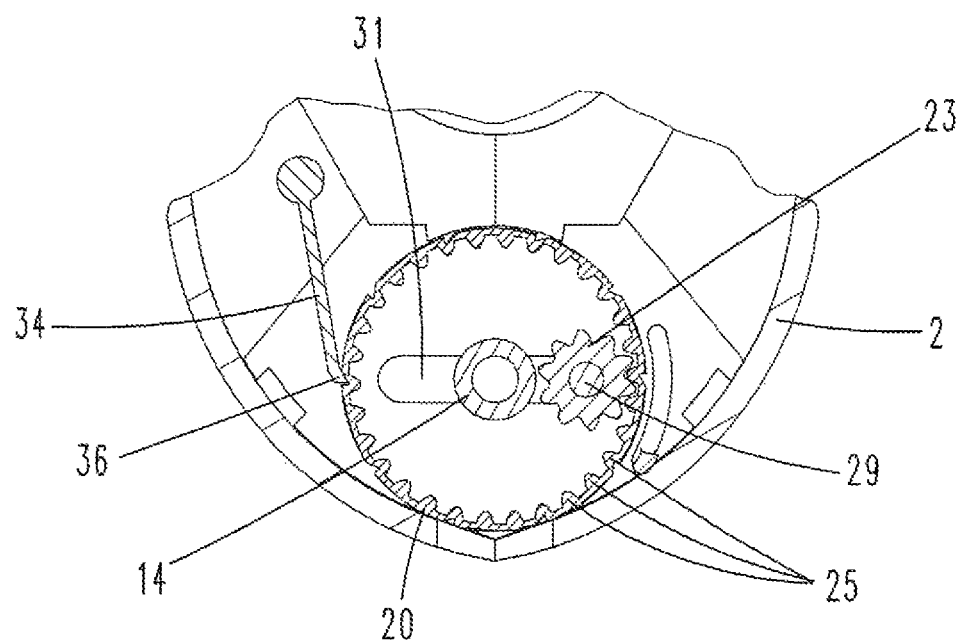
FIG. 13 shows a cross section through the object according to FIG. 7 along the line XIII-XIII.
Figure 29:
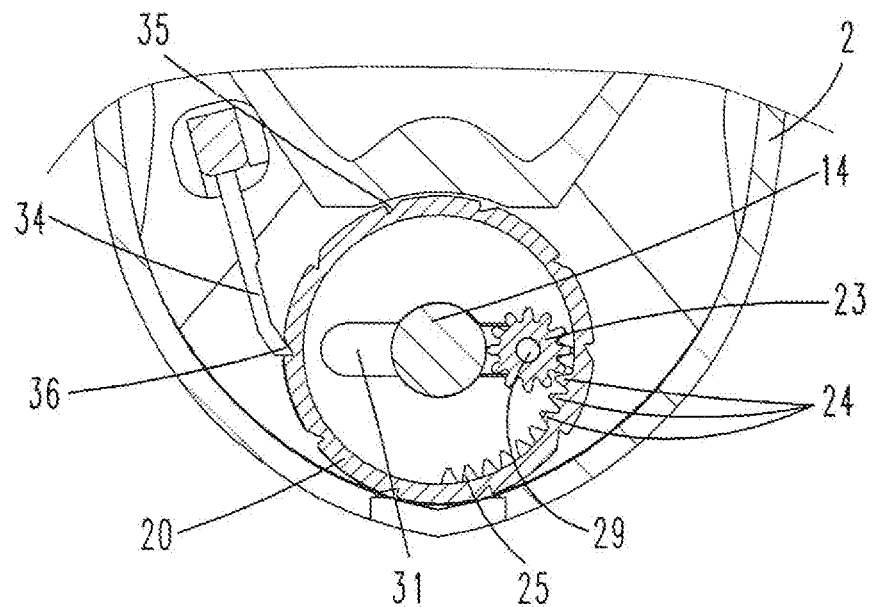
FIG. 29 shows a cross section through the object according to FIG. 25 in the plane XXIX-XXIX.
Figure 30:
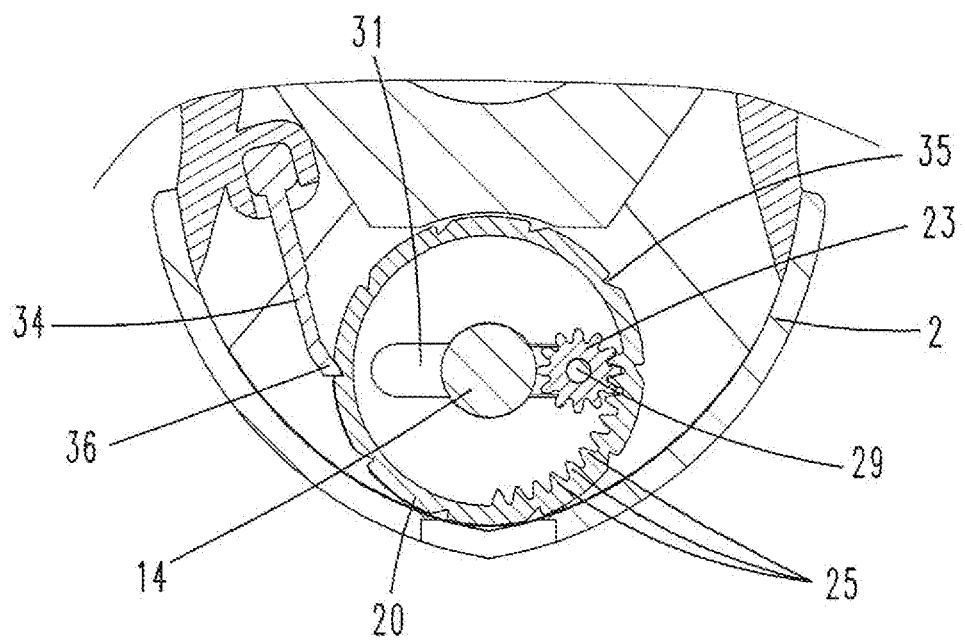
FIG. 30 shows a cross section through the object according to FIG. 25 along the line XXX-XXX.

This applies analogously to the cooperation between this (viewed from above) second counter wheel and the third counter wheel 20 located thereunder; see FIGS. 12 and 13.

With respect to FIGS. 14 and 15, it can also be gathered that the geometric axis A in fact extends laterally offset to the longitudinal axis L of the substance container 3 in the side view according to FIG. 14. Nevertheless, the bottom part or housing part 7 is arranged such that it vertically overlaps at least a substantial area of the substance container 3.

The drive part 10 likewise acts (as a counterforce) eccentrically upon the substance container 3 referred to the longitudinal axis L. In this case, the drive part 10 also does not cooperate with the first end face referred to the dispensing projection 8 of the substance container 3, but rather with a second end face, which is offset relative to the first end face in a stepped fashion and has a larger radius. This results in a more optimal utilization of the structural space for the counter 6.

The action and motion of the spring 19 acting upon the drive part 10 is described in greater detail below with reference to FIG. 16-20. In FIGS. 17 and 18, the drive part 10 is in its starting position. The substance container was not yet acted upon in this state.

In FIG. 19, the substance container 3 is pressed down (without showing an actuating finger of a user). This figure shows that the spring 19 has a more significant curvature and, according to FIG. 20, is altogether advanced with respect to the groove 40, in which a bottom region of the spring is accommodated, in the direction of the rotational motion of the drive part 10 in this groove 40 during such an actuation.

The following processes take place when the handheld device is used or the counter is actuated:

According to FIGS. 6 and 7, the drive part 10 contacts the end face 12 of the substance container 3 with a contact point 32 of the acting projection 11 in a starting position.

During an actuation of the handheld device, the user presses on the upper end face 33 of the substance container 3, for example, with a finger such that this substance container is moved downward in FIG. 6.

This causes the drive part 10 to be moved downward relative to the stationary rotational axis 14. Due to its cooperation with the slotted link 18, the slide block 17 causes a rotation of the drive part 10 relative to or about the rotational axis 14 during this process.

Engagement pins 21—in the exemplary embodiment two engagement pins—simultaneously penetrate into the engagement openings 22 of the uppermost counter wheel 20 in this case. They move into the engagement openings 22 until they contact an engagement face and then drive the corresponding counter wheel 20 in the circumferential direction, for example, by an angle of 36 degrees or 40 degrees. If the transmission gearwheel 23 comes in contact with the first gears 24 during this process, the additional counter wheel 20, which is located underneath the uppermost counter wheel and coupled to the transmission gearwheel 23, is also moved simultaneously. In special instances, the further counter wheel 20 located underneath the additional counter wheel is likewise moved simultaneously by means of the additional transmission gearwheel 23.

When the user releases the pressure upon the end face 33, the substance container 3 moves back into its starting position under the influence of a separate spring contained in the dispensing part.

The drive part 10 participates in this return motion due to the spring 19 acting upon the drive part such that it is subsequently once again in the state illustrated in FIG. 6.

During a rotation of a counter wheel 20, this counter wheel also passes an assigned reverse lock 34. For this purpose, the counter wheel is preferably provided with index notches 35 that extend in the direction of the geometric axis A of the rotational axis 14 and into which a reverse lock 34 engages with a frontal locking tab 36. In this way, a reverse rotation of the counter wheel 20 is prevented.

It is preferred that any or all of the aforementioned parts of the counter respectively consist of injection-molded plastic parts. They may be made, e.g., of PP or PE.

Another embodiment of the counter and of the handheld device is respectively described below with reference to FIGS. 21-32.

With respect to conforming aspects of the described embodiments, the description of certain parts, which are identified by the same reference symbols, is not repeated in its entirety. The preceding description of such parts accordingly also applies to the second embodiment. Vice versa, the description of parts with reference to the second embodiment also applies to parts with the same reference symbols in the first embodiment, which were not described or not described in every detail with reference to this first embodiment. Consequently, the description of the second embodiment accordingly also applies to the first embodiment as long as it does not concern a specific modification referred to the second embodiment.

According to FIG. 21, the counter is in this embodiment also connected to a bottom part, in this case a bottom plate 7, which simultaneously forms an outer side of the assembled housing 2 of the handheld device 1 on its side that faces away from the counter.

The exploded views in FIGS. 22 and 23 show that, in contrast to the first embodiment, the drive part 10 does not cooperate with the first rotational axis 14 in a geared fashion in order to realize the required rotational motion. In fact, it is preferred that only the acting part 49 cooperates with a slide block 42 fixed on the housing by means of the slotted link 41 realized on the outer side of the acting part 49; see, e.g., FIG. 31. The slide block 42 is preferably realized independently of the bottom plate 7. As in the first exemplary embodiment, it preferably forms an integral part of and consists of the same material as the housing or is at least rigidly connected to the housing 2. This connection is preferably produced in its region that is horizontally assigned to the dispensing projection 8 of the inserted substance container.

The spring 19 is preferably realized in the form of a spiral coiled spring. As such, it is preferably also arranged coaxial to the first rotational axis 14. It is particularly seated on a shoulder of the first rotational axis 14 as illustrated, e.g., in FIG. 24. A continuation section 44 of the first rotational axis 14 extends in such a way that it still overlaps the spring 19. On the other end, the spring 19 is seated on a holding pin 45 of the drive part 10, which in the assembled state extends coaxial to the first rotational axis 14 as illustrated, e.g., in FIG. 25; in this respect, see also FIG. 24.

In this embodiment, the drive part 10 can be displaced relative to the acting part 49 vertically, i.e. in the direction of the first rotational axis. In order to ensure the lower position required for rotationally actuating a counter wheel, the drive part 10 is arranged such that it cooperates with an additional spring 50. In the exemplary embodiment, the spring 50 is preferably supported on the inside of the acting part 49. The spring 50 is preferably realized integrally with and made of the same material as the drive part 10, particularly in the form of a plastic spring as shown.

The spring 19, in contrast, preferably consists of a metallic spring, particularly a steel spring.

The drive part 10 is realized in a sleeve-like fashion in a first region that is preferably arranged within the acting part 49. The drive part 10 also encompasses part of the axial extent of the spring 19 with this sleeve-like region. Viewed in the radial direction, the spring 19 is in this region arranged between the first rotational axis 14 and the drive part 10; see also FIG. 24.

The drive part 10 furthermore continues, in particular integrally, in the form of one or more shaped engagement sections, preferably two engagement sections as shown in the exemplary embodiment, wherein said shaped engagement sections are realized in the form of engagement pins 21 in this case. These shaped engagement sections preferably are also arranged opposite of one another with respect to a diameter line of the first rotational axis or of the sleeve-like region of the drive part as shown.

Figure 34:
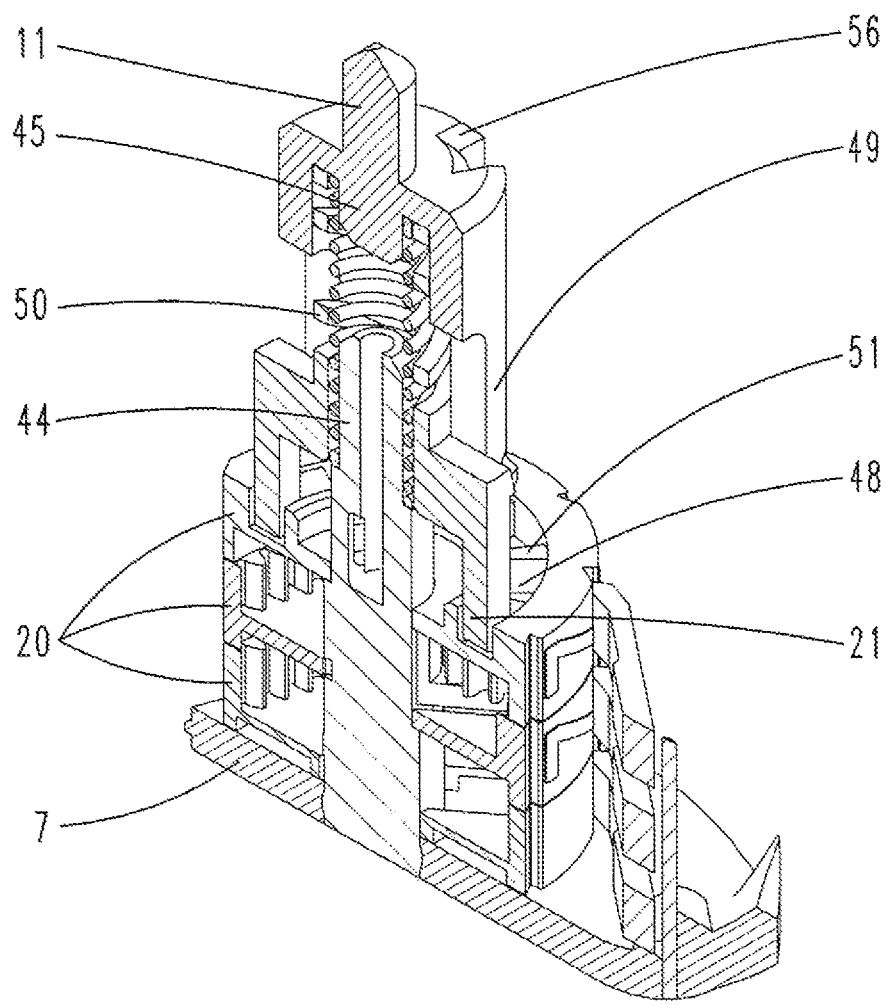
FIG. 34 shows an illustration according to FIG. 33 with a different rotational angle of the plane of section.

A shaped engagement section 21 respectively engages into an engagement opening 22 of the counter wheel. In this case, the shaped engagement section 21 contacts an engagement face 48, which preferably extends vertically, i.e. in the direction of the rotational axis, referred to the rotating direction of the counter wheel (see, e.g., FIG. 34). In this second exemplary embodiment, a counterface 51 provided opposite to the rotating direction preferably is realized in a curved fashion in any case. It forms a guide bevel for the shaped engagement section 21, which accordingly also rotates backward during a return stroke of the acting part and thereby moves into the next engagement opening 22. Due to the backward rotation and the movement past the guide bevel, the drive part 10 is in this case also raised in the required fashion, as well as subsequently pressed down again by the spring 50.

During this backward rotation, in particular, a relative motion between the acting part and the engagement part in the direction of the rotational axis accordingly takes place such that the aforementioned spring 50 is also advantageous in this respect.

The drive part 10 is preferably held on the acting part 49 in a captive fashion. For this purpose, a snap fitting may be provided as illustrated in FIG. 35. A locking tab 52 on the engagement part may be designed for moving over and engaging behind a complementary locking element 53 on the acting part (during the assembly). In order to realize the desired and required axial relative motion between the drive part 10 and the acting part 49, one longitudinal groove or preferably two longitudinal grooves 54 are provided on the acting part 49, in particular, opposite of one another as illustrated in the exemplary embodiment.

The reverse lock 34 comprises three finger-like locking elements that respectively feature a locking tab 36. The locking elements are rooted in a common holding section 46 that is preferably realized integrally with and made of the same material as the locking elements. The holding section 46 is rigidly connected to the bottom part 7, preferably by means of a plug-in connection. It is not rotatable relative to the bottom part 7 such that an elastic deflection of a reverse lock 34 occurs during a corresponding rotation of the assigned counter wheel.

Figure 32:
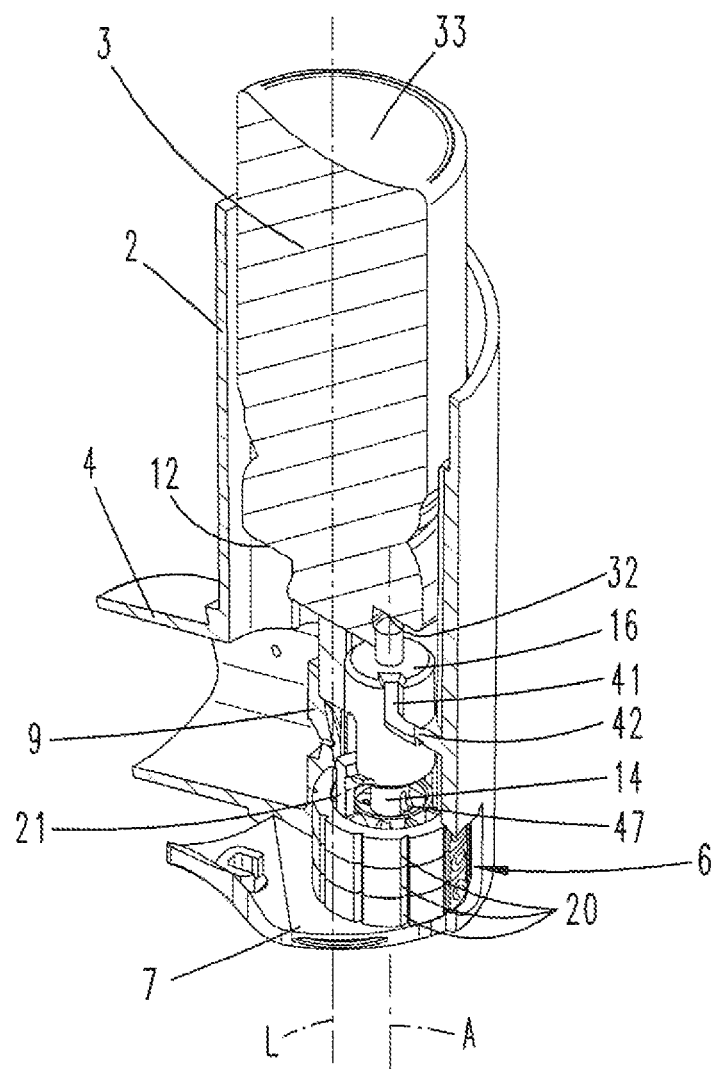
FIG. 32 shows a perspective view according to FIG. 31 in the form of an oblique top view.
Figure 33:
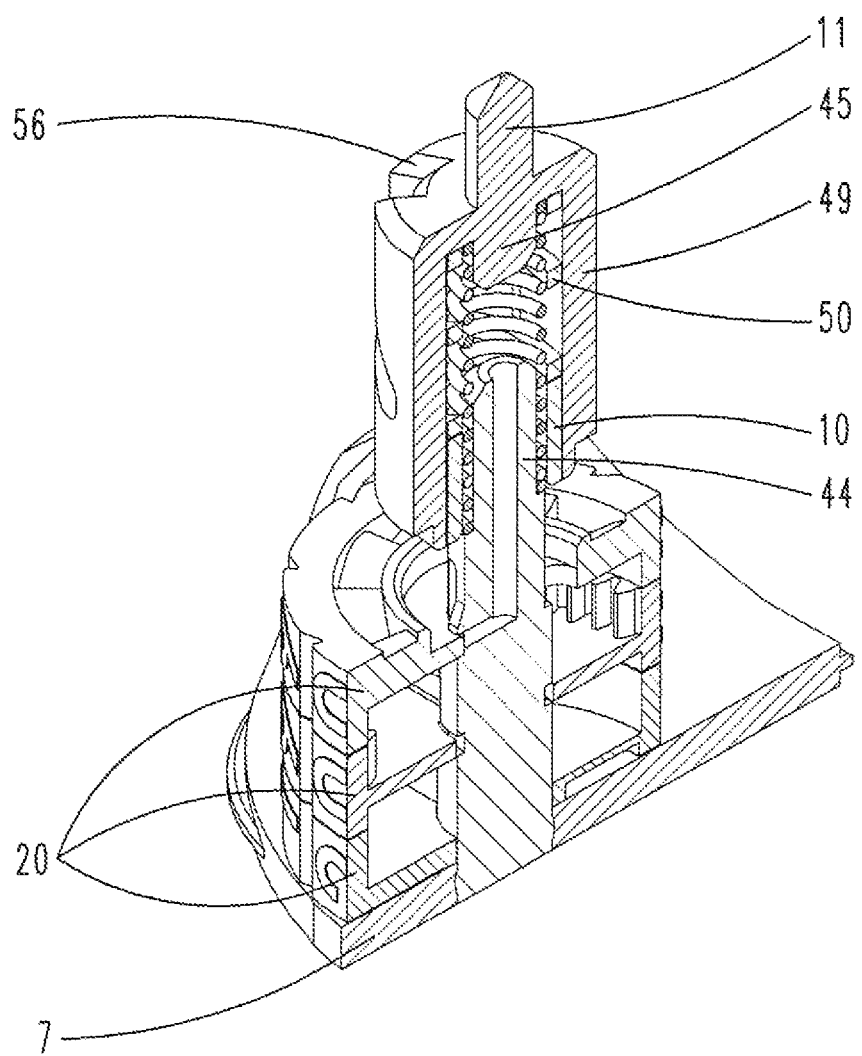
FIG. 33 shows an enlarged detail of the counter that is sectioned along a diameter line of the rotational axis.

An automatically engaging locking tab 47 is furthermore provided on the first rotational axis 14 such that the counter wheels are axially held in the assembled state; see, e.g., FIG. 32.

The following processes take place when the handheld device 1 according to the second embodiment is used:

The user presses on the upper end face 33 of the substance container 3, which is thereby pressed down relative to the housing 2. This presses down the acting part 49, which simultaneously carries out a rotational motion about its (vertical) longitudinal axis over part of this motion in the direction of the rotational axis due to the cooperation between the shaped gear section and the gear part.

The shaped gear section particularly consists of a slotted link 41 as illustrated, for example, in FIG. 32 and the gear part consists of a slide block 42 of the housing 2 that protrudes into the slotted link.

The figures furthermore show that the slotted link 41 is realized over part of its length in such a way that a rotation of the acting part occurs. The acting part 49 is displaced without such a rotation over the remaining length.

When the acting part 49 is pressed down, the spring 50 acting upon the drive part 10 is compressed. The drive part 10 thereby is displaced into its lower end position referred to the acting part 49 if this displacement has not already taken place such that it securely engages with the counter wheel.

Since the acting part simultaneously rotates when it is pressed down, a corresponding rotation of the drive part 10 and therefore of the (uppermost) counter wheel 20 accordingly takes place simultaneously.

After the user has once again released the substance container 3, this substance container moves back into its starting position under the influence of its internal spring. The acting part 49 directly follows this return motion due to the prestress of the spring 19. A backward rotation of the acting part 49 accordingly also takes place in this case as a result of the gear-like cooperation of the acting part with the housing 2.

Due to the rotational coupling with the drive part 10, this drive part also rotates backward simultaneously. The angular faces of the engagement openings in the counter wheel 20 make it possible for an engagement projection of the drive part 10 to penetrate into an oppositely arranged engagement opening (if applicable, after passing over several engagement openings).

Consequently, not only the acting part 49, but also the drive part 10 carries out a reciprocating rotational motion during an actuation cycle of the device.

The dose dispensed when the substance container is pressed down therefore is counted due to the rotational motion of the counter wheel taking place during the forward rotational motion of the drive part 10. The reverse lock prevents a backward rotation of the counter wheel while the drive part carries out the second part of the rotational motion, namely the backward rotational motion. Consequently, each dispensed dose is counted. The counter therefore consists of a counter for counting individual doses.

Figure 31:
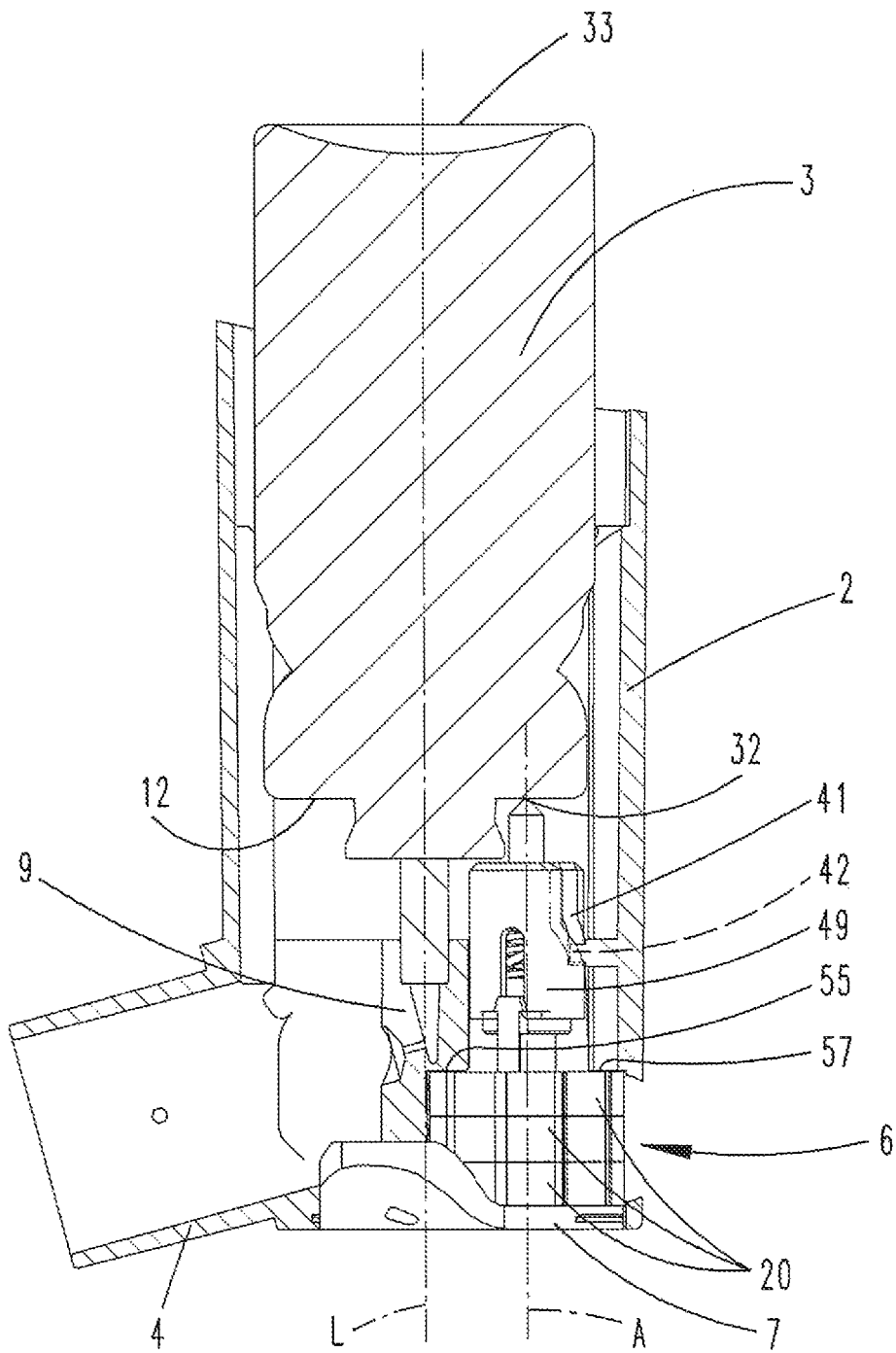
FIG. 31 shows a schematic sectioned side view of the handheld device with a counter arranged therein according to the additional embodiment.

FIG. 14 and FIG. 31 respectively show that the receptacle 9 forms a step 55, particularly on its side facing away from the nozzle 4, in both exemplary embodiments, wherein said step creates the space for accommodating the receptacle 9 for the counter wheels 20 such that the structural space of the housing 2 is advantageously utilized. This can also be gathered from the cross-sectional illustrations, e.g., in FIGS. 9, 8, 20 and 26. In the second embodiment, a step 57 is additionally or alternatively provided on the side of the housing, wherein this step can, in principle, also be alternatively or additionally realized in the first embodiment.

The user can read the number of dispensed doses or, when counting down, the number of remaining doses on the rear side of the housing or on the side facing away from the nozzle 4; see, e.g., FIG. 8. The numbers are shown in such a way that they can be read in the longitudinal direction of the housing or the substance container 3. For this purpose, an opening 58 is provided in the housing. The legible characters of the counter wheel or the multiple counter wheels are visible through the opening 58 that is preferably realized in the form of an elongated hole. The opening may be filled with a transparent part. However, it may also be realized in the form of a clear opening and insofar allow direct access to the one or more counter wheel/wheels.

With respect to the reverse lock 34, which preferably comprises a separate locking finger for each counter wheel 20 as shown, it is proposed that this reverse lock cooperates with an outer circumferential surface of a counter wheel 20, on which the legible characters are also arranged. For this purpose, the outer circumferential surface particularly features index notches 35 that extend in the direction of the first rotational axis and into which a locking tab 36 of the reverse lock 34 engages at a standstill. An index notch 35 is illustrated, e.g., in FIGS. 9-13 and 27-30 and features a shallow flank, over which the locking tab can pass, as well as a steep flank that essentially extends along a diameter line (cross-sectional illustration).

The latter flank prevents a backward rotation whereas the locking tab can pass over the former flank.

The second gears 25 preferably are always realized over the entire circumference of the corresponding surface. However, they may also be realized over part of the surface only as illustrated in FIG. 22, e.g. if the potential range of numerals actually is not fully utilized for the counter. This applies analogously to the legible characters that preferably consist of such numerals.

The counter particularly can also be easily assembled. The first rotational axis and/or rotational lock 34 initially can be attached to the bottom part 7 from above by means of plug-in assembly. The first rotational axis 14 preferably is realized in one piece with the second rotational axes 29.

One or more counter wheels, preferably three counter wheels as illustrated in the exemplary embodiments, can then be attached to the first rotational axis 14. They are simultaneously secured by the locking tab 47 in the second embodiment, but optionally also in the first embodiment.

After the installation of the lower or the two lower counter wheels, the transmission gearwheel respectively needs to be installed on the second rotational axis 29 by means of plug-in assembly.

In the second embodiment, the spring 19, as well as the drive part 10 and the acting part 49, can then be attached to the first rotational axis 14. The acting part 49 is interlocked with the drive part 10 by pressing down the acting part. Alternatively, the two parts can also be interlocked beforehand and attached in assembled form.

In the first embodiment, the drive part 10 and the acting part 49 are realized in the form of a unit such that only one installation process is required in this case.

The thusly assembled counter can then be inserted into the housing 2 from below. Since the bottom part 7 is advantageously realized larger than necessary for the mere installation of the counter, it can also be comfortably handled, particularly for the installation into the housing 2, when the counter is already installed thereon. An advantageous alignment option is thereby also realized. The acting part 49 in combination with the drive part 10 can during the preassembly be aligned in such a way that the—preferably dual, oppositely arranged—slotted links 41 are aligned with the slide blocks 42. In order to compensate slight alignment inaccuracies, the slotted links 41 are preferably provided with an insertion bevel 56 that widens in the circumferential direction of the acting part 49; see, e.g., FIG. 34.

Locking tabs 56 may also be provided on the bottom part as shown in order to snap-fit the bottom part.

With the exception of the reverse lock 34, all parts of the counter are connected to or guided on the first rotational axis 14.

The preceding explanations serve for elucidating all inventions that are included in this application and respectively enhance the prior art independently with at least the following combinations of characteristics, namely:

A counter, which is characterized in that the acting part 49 is rotationally moved and connected to the drive part 10 in order to rotate jointly therewith.

A counter, which is characterized in that the rotational motion of the acting part 49 is superimposed with a motion in the direction of the rotational axis 14 and/or that the drive part 10 and/or the acting part 49 feature a shaped gear section, wherein the shaped gear section is preferably designed for cooperating with a gear part provided on the rotational axis 14 or separately of the rotational axis 14.

A counter, which is characterized in that the drive part 10 is arranged coaxial to the rotational axis 14 and/or that the drive part 10 is completely separated from the counter wheel 20 prior to a displacement and/or that the drive part 10 is also captured on the (first) rotational axis 14 prior to a displacement and/or that the shaped gear sections consist of a slotted link 18 on one of the components drive part 10 and (first) rotational axis 14, as well as a slide block 17 on the other of the components drive part 10 and (first) rotational axis 14 and/or that the counter 6 comprises a bottom part 7 that, if applicable, forms part of a housing of the handheld device 1.

A counter, which is characterized in that a spring 19 acting upon the drive part 10 and/or the acting part 9 is supported on an inner side of the bottom part 7, wherein the first rotational axis 14 preferably is rigidly connected to the bottom part 7, and/or that several counter wheels 20 are provided, wherein all counter wheels 20 preferably are arranged coaxial, and/or that the drive part 10 features a shaped engagement section in the form of an engagement pin 21, wherein a shaped engagement section furthermore preferably extends axially parallel to the rotational axis 14.

A counter, which is characterized in that a counter wheel 20 directly assigned to the drive part 10 features an engagement opening 22, wherein the engagement opening 22 is preferably designed and arranged for accommodating a shaped engagement section, and/or that a transmission gearwheel 23 is provided between two counter wheels 20 that are arranged directly adjacent to one another in the direction of the rotational axis 14, wherein said transmission gearwheel extends transverse to its (second) rotational axis 29 such that it overlaps both counter wheels 20.

A counter, which is characterized in that a transmission gearwheel 22 is rotatably held on a radial arm 30 of the first rotational axis 14, wherein two transmission gearwheels 23 and/or two radial arms 30 are preferably provided, and wherein the radial arms 30 are preferably spaced apart in the direction of the first rotational axis 14.

A counter, which is characterized in that a spring 19, which generates the spring force for the drive part 10 and/or the acting part 49, extends laterally of a counter wheel 20 and in the direction of the first rotational axis 14 such that it overlaps the counter wheel 20 and/or that one or more of the counter wheels 20 cooperate with a reverse lock 34, wherein a reverse lock 34 is preferably realized in the form of a locking part that acts upon an outer circumferential surface of a counter wheel 20 featuring the characters, wherein a motion plane of the locking part furthermore preferably extends transverse to the first rotational axis 14 and/or the locking part is fixed on the bottom part 7.

A handheld device, which is characterized in that the counter 6 features a bottom part 7, which may form part of the housing 2 and can be inserted therein, wherein the bottom part 7 at least partially overlaps the substance container 3 in the direction of the longitudinal axis L thereof, and that the bottom part 7 carries a stationary (first) rotational axis 14 for the counter wheel 6, on which the drive part 10 is preferably also guided, wherein the drive part 10 is located on the side of the substance container 3 referred to the counter wheel 20.

A handheld device, which is characterized in that the drive part 10 and/or the acting part 9 feature a shaped gear section for cooperating with a stationary gear part of the housing in order to realize a rotational motion of the drive part 10 relative to the housing 2 during the course of the dispensing stroke.

LIST OF REFERENCE SYMBOLS

1 Handheld device
2 Housing
3 Substance container
4 Dispensing nozzle
5 Protective cap
6 Counter 7 Bottom part
8 Dispensing projection
9 Receptacle
10 Drive part
11 Acting projection
12 End face
13 Guide section
14 First rotational axis
15 End face
16 End face
17 Slide block
18 Slotted link
19 Spring
20 Counter wheel
21 Engagement pin
22 Engagement opening
23 Transmission gearwheel
24 First gears
25 Second gears
26 Bottom
27 Circumferential surface area section
28 Character
29 Second rotational axis
30 Radial arm
31 Opening
32 Contact point
33 Upper end face
34 Reverse lock
35 Index notch
36 Locking tab
37 Insertion section
38 Rotary section
39 Slotted link surface
40 Groove
41 Slotted link
42 Slide block
43 Shoulder
44 Continuation section
45 Holding pin
46 Holding section
47 Locking tab
48 Engagement face
49 Acting part
50 Spring
51 Counterface
52 Locking tab
53 Complementary locking element
54 Longitudinal groove
55 Step
56 Insertion bevel
57 Step
58 Opening
A Geometric axis
L Longitudinal axis

The invention claimed is:

1. A counter (6) for a handheld device (1) for dispensing pharmaceutical substances, with at least one counter wheel (20) that features legible characters, wherein the counter wheel (20) is rotatable about a rotational axis (14) and a drive part (10) for the counter wheel (20) is provided in order to rotationally act upon the counter wheel (20), wherein said drive part (10) features a shaped engagement section for cooperating with the counter wheel (20), and wherein an acting part (49) is furthermore provided and is configured to be displaced relative to the counter wheel (20) in the direction of the rotational axis (14) against a spring force, wherein the acting part (49) is rotationally moved and connected to the drive part (10) in order to rotate jointly therewith, and wherein the drive part (10) features a guide section (13), by which it is seated on the rotational axis (14) of the counter in the assembled state of the counter (6), wherein the rotational axis of the counter is realized in the form of a stationary pin, wherein the drive part (10) and/or the acting part (49) feature a shaped gear section, and wherein the shaped gear section comprises a slotted link (18) on one of the drive part (10) and rotational axis (14), as well as a slide block (17) on the other of the drive part (10) and rotational axis (14).

2. The counter according to claim 1, wherein a rotational motion of the acting part (49) is superimposed with a motion in the direction of the rotational axis (14).

3. The counter according to claim 1, wherein the shaped gear section is designed for cooperating with a gear part provided on the rotational axis (14) or separately of the rotational axis (14).

4. The counter according to claim 1, wherein the drive part (10) is arranged coaxial to the rotational axis (14).

5. The counter according to claim 1, wherein the drive part (10) is completely separated from the counter wheel (20) prior to a displacement.

6. The counter according to claim 1, wherein the drive part (10) is also coaxial with the rotational axis (14) prior to a displacement.

7. The counter according to claim 1, wherein the counter (6) comprises a bottom part (7) that forms part of a housing of the handheld device (1).

8. The counter according to claim 7, wherein a spring (19) acting upon the drive part (10) and/or the acting part (9) is supported on an inner side of the bottom part (7).

9. The counter according to claim 7, wherein the rotational axis (14) is rigidly connected to the bottom part (7).

10. The counter according to claim 1, wherein several counter wheels (20) are provided.

11. The counter according to claim 10, wherein all counter wheels (20) are arranged coaxial.

12. The counter according to claim 1, wherein the drive part (10) features a shaped engagement section in the form of an engagement pin (21).

13. The counter according to claim 1, wherein a shaped engagement section extends axially parallel to the rotational axis (14).

14. The counter according to claim 1, wherein a counter wheel (20) directly assigned to the drive part (10) features an engagement opening (22).

15. The counter according to claim 14, wherein the engagement opening (22) is designed and arranged for accommodating a shaped engagement section.

16. The counter according to claim 1, wherein a transmission gearwheel (23) is provided between two counter wheels (20) that are arranged directly adjacent to one another in the direction of the rotational axis (14), wherein said transmission gearwheel extends transverse to a second rotational axis (29) such that it overlaps both counter wheels (20).

17. The counter according to claim 16, wherein a transmission gearwheel (22) is rotatably held on a radial arm (30) of the rotational axis (14).

18. The counter according to claim 16, wherein two transmission gearwheels (23) are provided.

19. The counter according to claim 17, wherein two radial arms (30) are provided.

20. The counter according to claim 19, wherein the radial arms (30) are spaced apart in the direction of the rotational axis (14).

21. The counter according to claim 1, wherein a spring (19), which generates the spring force for the drive part (10) and/or the acting part (49), extends laterally of a counter wheel (20) and in the direction of the rotational axis (14) such that it overlaps the counter wheel (20).

22. The counter according to claim 1, wherein one or more of the counter wheels (20) cooperate with a reverse lock (34).

23. The counter according to claim 22, wherein a reverse lock (34) is realized in the form of a locking part that acts upon an outer circumferential surface of a counter wheel (20) featuring the characters.

24. The counter according to claim 23, wherein a motion plane of the locking part extends transverse to the rotational axis (14) and/or the locking part is fixed on a bottom part (7) of the counter.

\* \* \* \* \*